United States Patent
Nardo et al.

(10) Patent No.: US 8,932,547 B2
(45) Date of Patent: Jan. 13, 2015

(54) MODULAR PLANT FOR REMOVAL OF POLLUTANTS FROM FLUE GASES PRODUCED BY INDUSTRIAL PROCESSES

(75) Inventors: Tommaso Nardo, Rome (IT); Antonio Maria Nardo, Rome (IT); Angelo Basile, Calabria (IT); Fausto Gallucci, Calabria (IT)

(73) Assignee: AST Engineering S.R.L., Rome (IT)

( * ) Notice: Subject to any disclaimer, the term of this patent is extended or adjusted under 35 U.S.C. 154(b) by 1295 days.

(21) Appl. No.: 12/674,223

(22) PCT Filed: Aug. 20, 2008

(86) PCT No.: PCT/IT2008/000559
§ 371 (c)(1),
(2), (4) Date: Sep. 27, 2010

(87) PCT Pub. No.: WO2009/025003
PCT Pub. Date: Feb. 26, 2009

(65) Prior Publication Data
US 2011/0288184 A1   Nov. 24, 2011

(30) Foreign Application Priority Data
Aug. 20, 2007 (IT) .............................. RM2007A0446

(51) Int. Cl.
| | | |
|---|---|---|
| *B01D 47/00* | (2006.01) | |
| *C01B 17/20* | (2006.01) | |
| *C01B 17/16* | (2006.01) | |
| *C01B 17/00* | (2006.01) | |
| *C07C 27/00* | (2006.01) | |
| *G01D 11/26* | (2006.01) | |
| *B01D 50/00* | (2006.01) | |
| *B01D 53/22* | (2006.01) | |
| *C01B 3/06* | (2006.01) | |
| *E04H 5/02* | (2006.01) | |
| *B01D 53/75* | (2006.01) | |
| *C07C 29/152* | (2006.01) | |
| *B03C 3/017* | (2006.01) | |
| *B01D 53/86* | (2006.01) | |
| *B01D 53/77* | (2006.01) | |

(52) U.S. Cl.
CPC .......... *E04H 5/02* (2013.01); *C01B 2203/0485* (2013.01); *Y02C 10/04* (2013.01); *B01D 53/86* (2013.01); *B01D 2257/404* (2013.01); *B01D 2257/504* (2013.01); *B01D 53/77* (2013.01); *B01D 2257/2047* (2013.01); *Y02C 10/06* (2013.01); *B01D 53/229* (2013.01); *C01B 3/068* (2013.01); *Y02E 60/36* (2013.01); *B01D 53/75* (2013.01); *Y02C 10/10* (2013.01); *B01D 2251/404* (2013.01); *B01D 2257/7027* (2013.01); *C07C 29/152* (2013.01); *B01D 2257/602* (2013.01); *B03C 3/017* (2013.01); *B01D 2257/2045* (2013.01); *B01J 2219/0002* (2013.01); *B01D 2256/16* (2013.01); *B01D 2257/302* (2013.01)
USPC ........ 423/220; 423/210; 423/235; 423/239.1; 423/242.7; 423/242.1; 423/400; 423/648.1; 518/700

(58) Field of Classification Search
USPC ............ 518/700; 423/235, 400, 648.1, 242.7, 423/210, 220, 239.1, 242.1; 422/119, 170
See application file for complete search history.

(56) References Cited

U.S. PATENT DOCUMENTS

| | | | |
|---|---|---|---|
| 4,071,602 A | 1/1978 | Pearce | |
| 4,089,940 A | 5/1978 | Norman et al. | |
| 4,985,217 A | 1/1991 | Schmid | |
| 4,986,966 A | 1/1991 | Lehto | |
| 5,254,155 A | 10/1993 | Mensi | |
| 5,305,574 A | 4/1994 | Fedock et al. | |
| 5,925,326 A | 7/1999 | Kapoor et al. | |
| 6,110,256 A | 8/2000 | Reynolds et al. | |
| 6,193,782 B1 | 2/2001 | Ray | |
| 6,342,169 B1 | 1/2002 | Hakka et al. | |
| 2002/0189444 A1 | 12/2002 | Brennecke et al. | |

(Continued)

FOREIGN PATENT DOCUMENTS

| | | |
|---|---|---|
| DE | 4235125 | 4/1994 |
| DE | 4309460 | 9/1994 |

(Continued)

OTHER PUBLICATIONS

International Search Report for PCT publication No. WO2009025003 dated Sep. 17, 2009.

(Continued)

*Primary Examiner* — Jafar Parsa
(74) *Attorney, Agent, or Firm* — Smith, Gambrell & Russell LLP

(57) ABSTRACT

The invention relates to a so-called zero emission 'AST-CNR/ITM system' modular plant for removal of pollutants from flue gases produced by industrial processes. The plant comprises prefabricated modular elements with programmed and automatic operation, easy to mount and assemble on site without undergoing expensive plant stoppage. Each module or 'reaction tower' comprises a plurality of sections vertically arranged on top of one another, which carry out the following functions: Removal of particulate matter with treatment and removal of chemical pollutants, such as heavy metals, chlorides, fluorides Treatment and removal of SOx Treatment and removal of NOx Capture of $CO_2$ Production of hydrogen Production of methanol. The various sections may be combined according to the requirements of the plant and of the flue gases to be treated.

33 Claims, 20 Drawing Sheets

(56) References Cited

U.S. PATENT DOCUMENTS

| | | |
|---|---|---|
| 2003/0045756 A1 | 3/2003 | Mimura et al. |
| 2004/0139853 A1 | 7/2004 | Bologa et al. |
| 2005/0214187 A1 | 9/2005 | Johnson |
| 2006/0261265 A1 | 11/2006 | Ray et al. |

FOREIGN PATENT DOCUMENTS

| | | |
|---|---|---|
| EP | 0740963 | 11/1996 |
| EP | 1552874 | 7/2005 |
| EP | 1642864 | 4/2006 |
| GB | 1493226 | 11/1977 |
| GB | 2098186 | 11/1982 |
| JP | 11081728 | 3/1999 |
| WO | 9518664 | 7/1995 |
| WO | 9853900 | 12/1998 |

OTHER PUBLICATIONS

Robert H. Perry, Perry's Chemical Engineer's Handbook, 6$^{th}$ edition, 1984, Fig. 20-102.

F. Gallucci, et al. "An experimental study of $CO_2$ hydrogenation into methanol involving a zeolite membrane reactor", Chemical Engineering and Processing vol. 43, Dec. 13, 2003, pp. 1029-1036.

PLANT BLOCK DIAGRAM

Figure 1.1
Flue gas cleaning block

Figure 1.2
CO2 Capture block

Figure 1.3
Hydrogen production block

Figure 1.4
Methanol production block

BLOCK 1.1 FLUE GAS WASHING 2.1 First section of the reaction tower - treatment of particulates
2.2 Second section of the reaction tower - FGD desulphurisation
2.3 Third section of the reaction tower - DeNox denitrification treatment FIGURE 3
BLOCK 1.2 CO2 CAPTURE
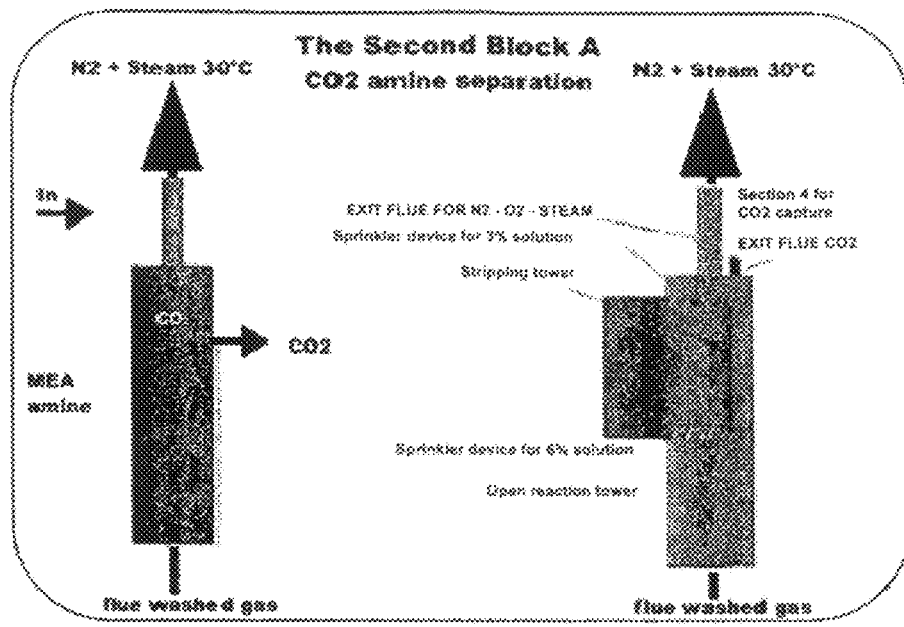
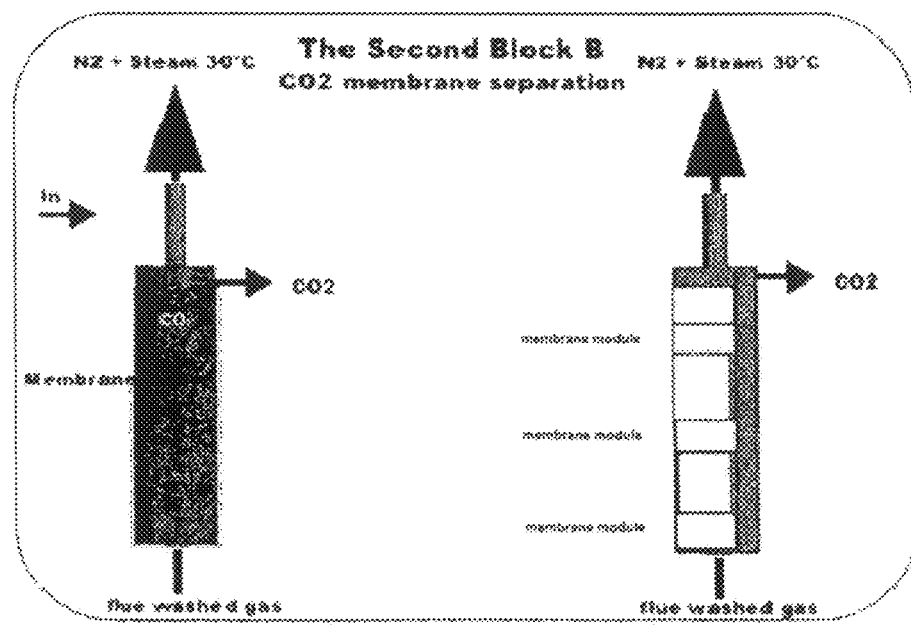
Figure 3.1 - CO2 separation with amine and heat stripping of the solution for CO2 separation
Figure 3.2 - CO2 membrane separation

FIGURE 4
BLOCK 1.3 HYDROGEN PRODUCTION
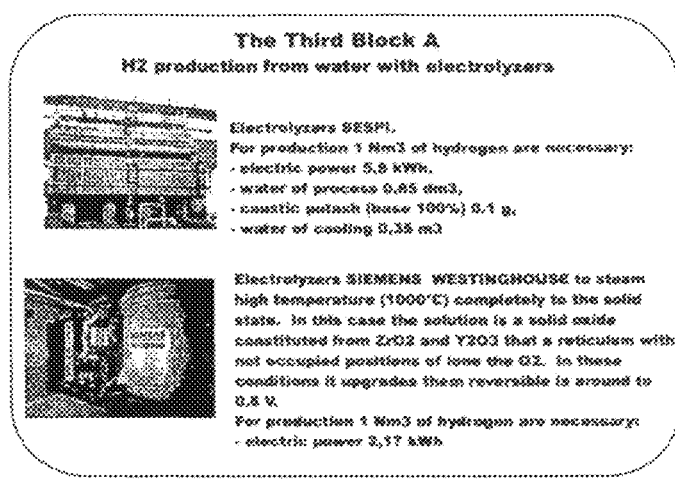
Figure 4.1 Hydrogen production with low temperature electrolysers
Figure 4.2 Hydrogen production with high temperature electrolyses
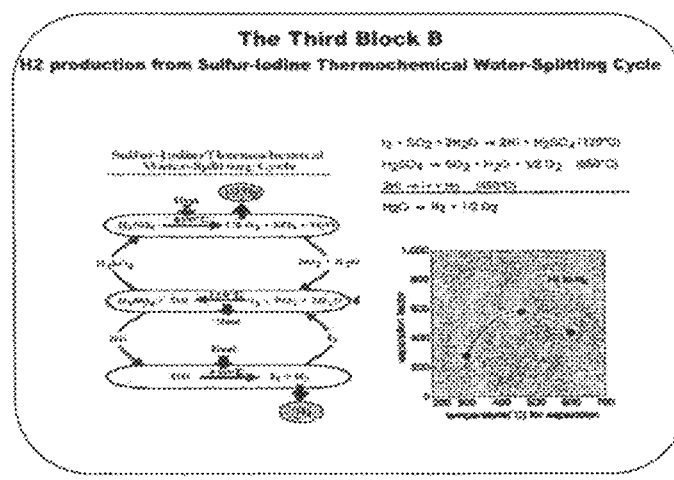
Figure 4.3 Hydrogen production by thermochemical water splitting

FIGURE 5
BLOCK 1.4 ETHANOL PRODUCTION
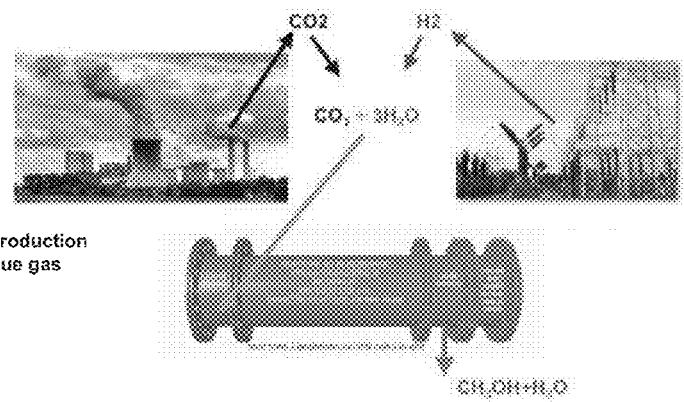
Figure 5.1
Methanol production using the flue gas from CO2
Figure 5.2
Methanol production using electric energy for hydrogen production
Figure 5.3
Methanol production in membrane reactors by catalytic reaction of hydrogen and CO2
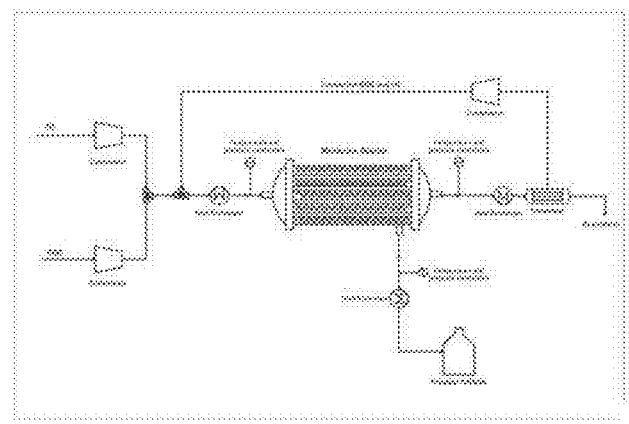
Figure 5.4
Diagram of methanol production by membrane reactors from hydrogen and CO2

FIGURE 6
REACTION TOWER CONFIGURATIONS THEREOF

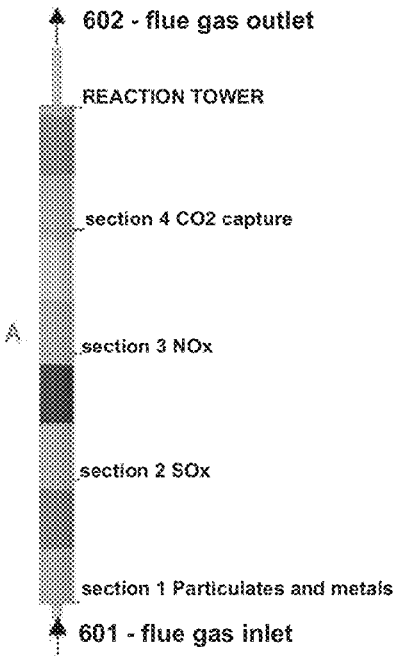

Figure 6.1
Reaction tower composed of four sections for removal of: metals and particulates SOx - NOx - CO2

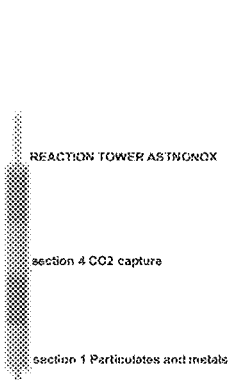 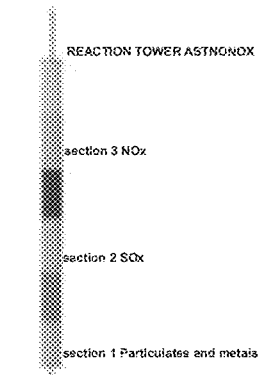 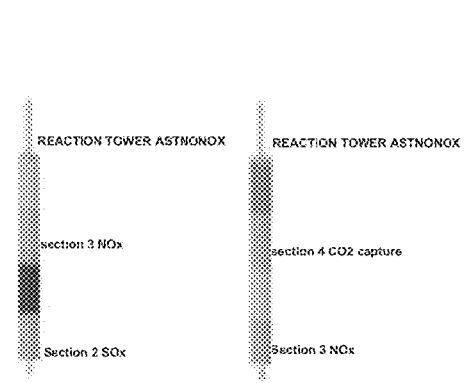 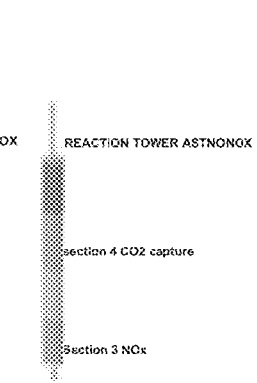

Different compositions of reaction tower based on the pollutants to be removed

601 - Flue gas inlet to the reaction tower
602 - Flue gas outlet from the reaction tower after washing and CO2 separation
6.2 - Tower composed of section 1 and 4 (metal removal and CO2 separation)
6.3 - Tower composed of section 1, 2 and 3 (metal removal, deSOx and deNOx)
6.4 - Tower composed of section 2 and 3 (deSOx and deNOx)
6.5 - Tower composed of section 4 and 4 (deSOx and CO2 separation)

FIGURE 7
PLANT UNIT MODULE
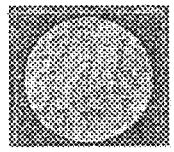
Figure 7.1
Figure 7.2
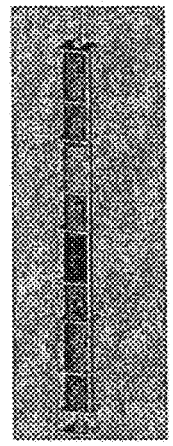
Figure 7.3

FIGURE 8
Plant assembly steps

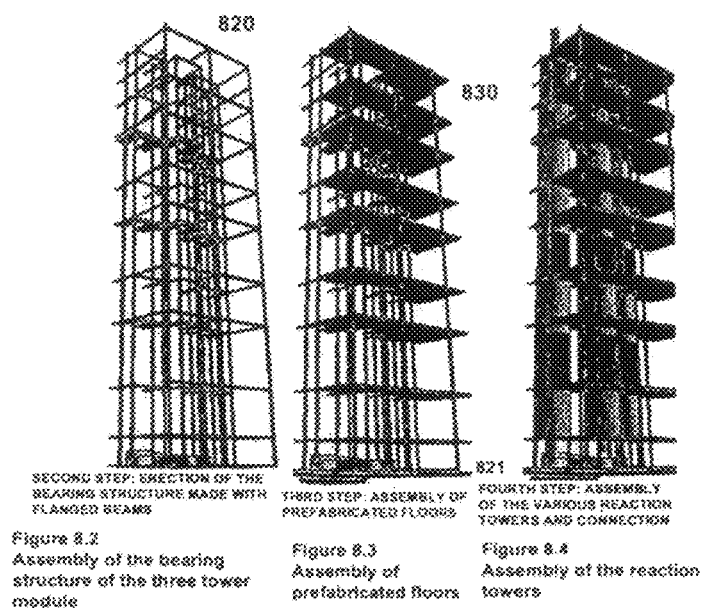

SECOND STEP: ERECTION OF THE
BEARING STRUCTURE MADE WITH
FLANGED BEAMS

THIRD STEP: ASSEMBLY OF
PREFABRICATED FLOORS

FOURTH STEP: ASSEMBLY
OF THE VARIOUS REACTION
TOWERS AND CONNECTION

Figure 8.2
Assembly of the bearing
structure of the three tower
module

Figure 8.3
Assembly of
prefabricated floors

Figure 8.4
Assembly of the reaction
towers

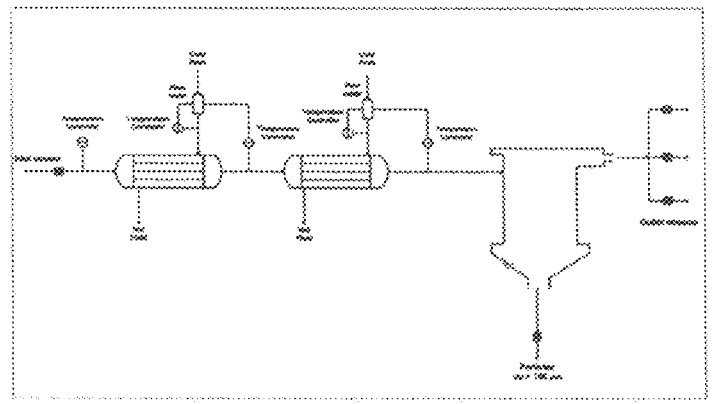

Figure 8.1
Assembly diagram of the flue gas distribution plant

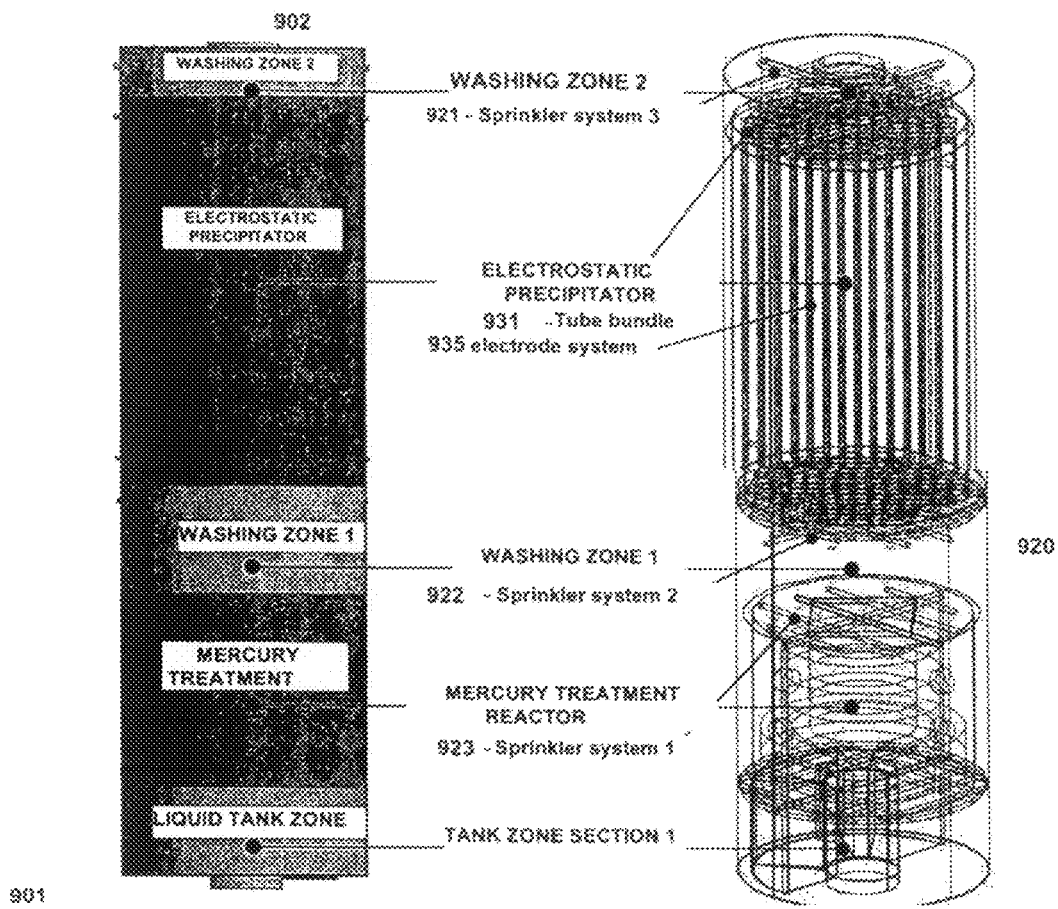
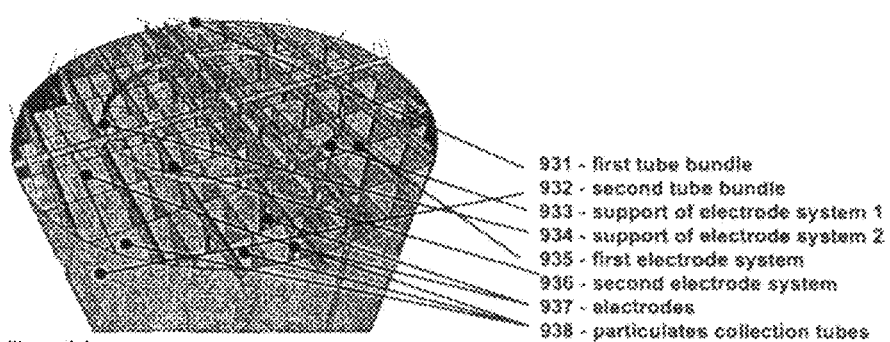

FIGURE 10
SECTION 1 OF REACTION TOWER

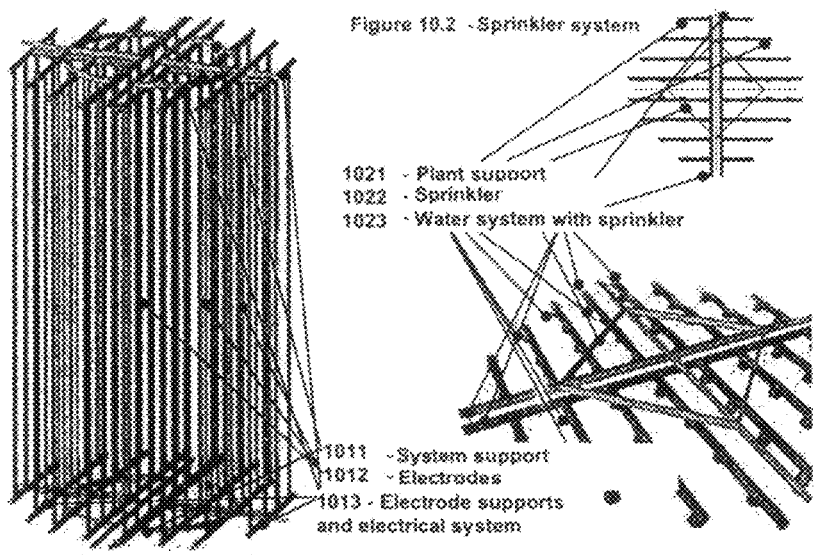

Figure 10.2 - Sprinkler system

1021 - Plant support
1022 - Sprinkler
1023 - Water system with sprinkler

1011 - System support
1012 - Electrodes
1013 - Electrode supports and electrical system Figure 10.1 - Electrostatic precipitator electrode system Figure 10.3 - Sprinkler system front

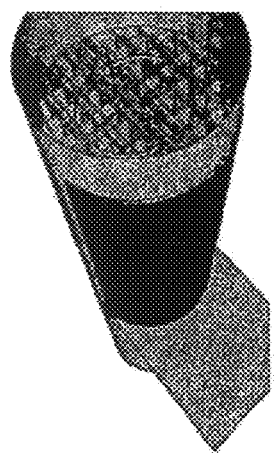

Figure 10.4 - Top view of sect. 1 only 2 tube bundles and closed skirt

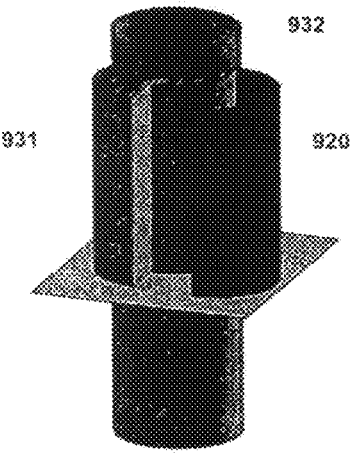

Figure 10.5 - View of sect. 1 open skirt with extraction of a tube bundle for repair purposes FIGURE 11
SECTION 1 OF REACTOR TOWER FOR MERCURY REMOVAL
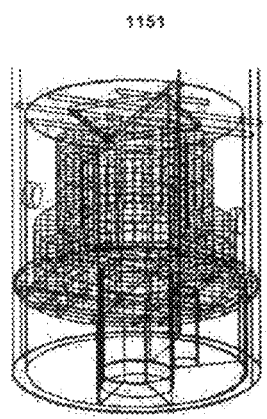
Figure 11.1
Perspective view of mercury reactor equipment
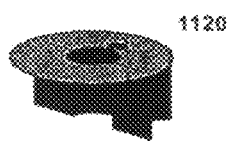
Figure 11.2
Mercury reactor tanks and support surface
Figure 11.3
Reactor ceramic cylinders
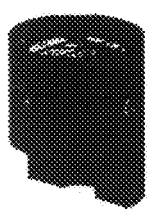
Figure 11.4
Mercury reactor mounted with skirt in a concentric position at the distance of 5.00 cm from the skirt of section 1 and only lacking the top skirt closure to be complete FIGURE 12
SECTION 2 REACTION TOWER
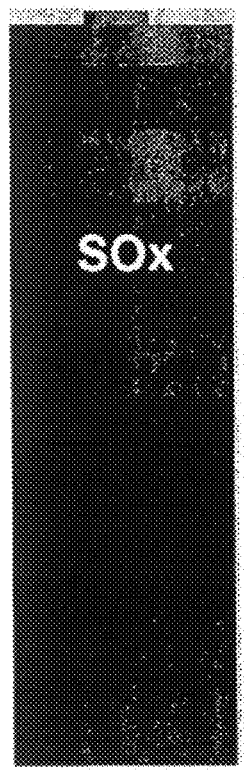
Figure 12.1
Section 2 of reaction
tower for
desulphurisation
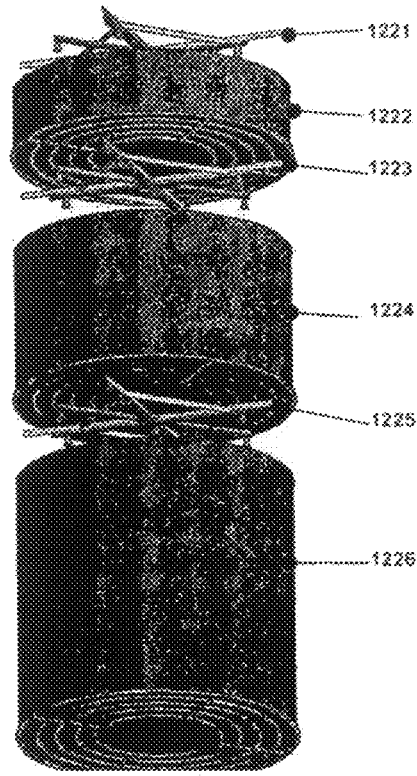
Figure 12.2
Reaction tower equipment
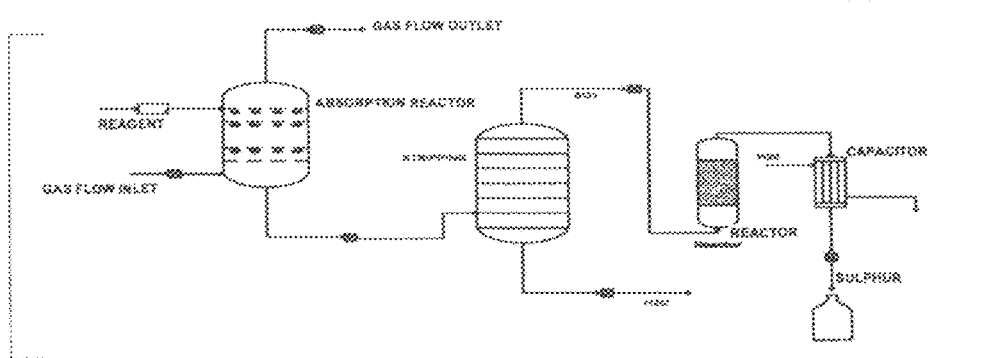
Figure 12.3
Desulphurisation plant diagram
1221 - Upper sprinkler plant
1222 - Upper catalyst pack
1223 - Median sprinkler plant
1224 - Median catalyst pack
1225 - Lower sprinkler plant
1226 - Lower catalyst pack FIGURE 13
SECTION 3 - REACTION TOWER
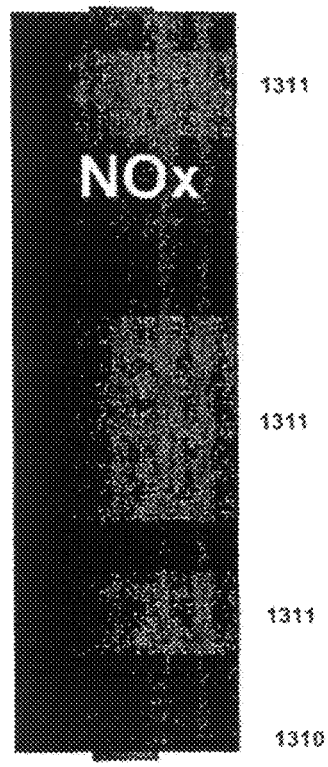
Figure 13.1
Section 3 - Reaction tower for deNox
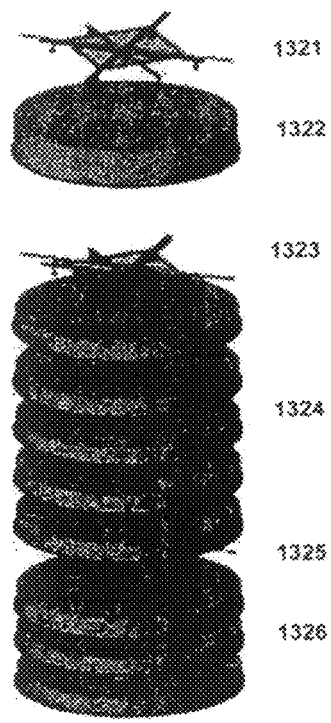
Figure 13.2
Equipment of section 3
1311 - Opening parts of the skirt to access the equipment
1321 - Upper sprinkler plant
1322 - Catalyst upper pack
1323 - Median sprinkler plant
1324 - Catalyst median packs
1325 - Lower sprinkler plant
1326 - Catalyst lower packs

FIGURE 14
SECTION 4 - REACTION TOWER

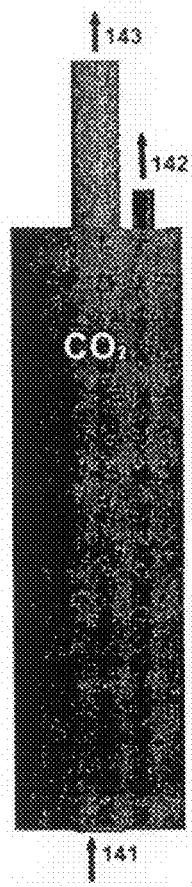
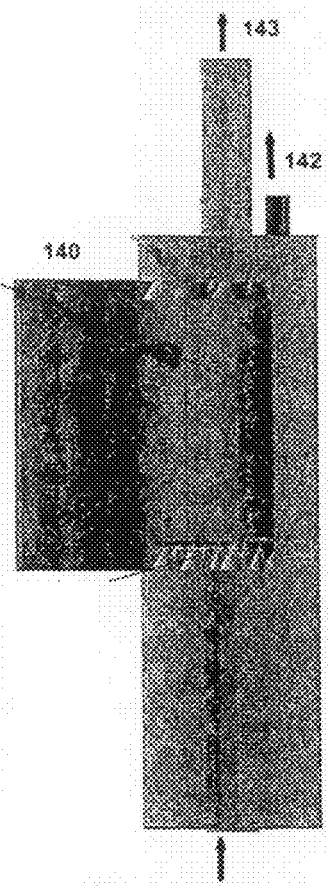
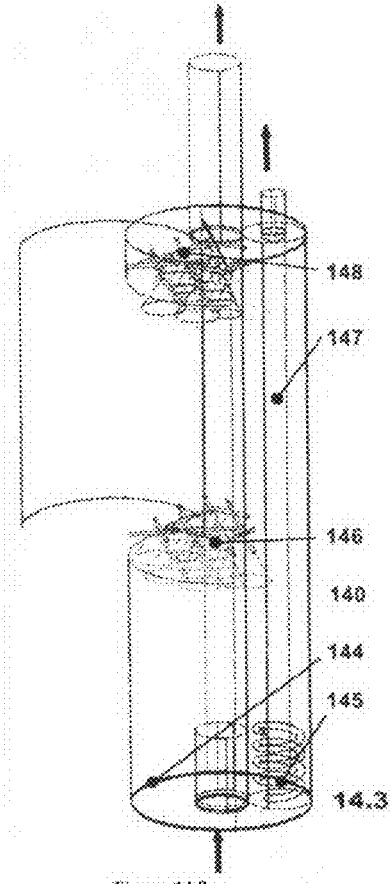

Figure 14.1
Absorbent reactor for capturing CO2 contained in the plant flue gas

Figure 14.2
Reactor with open skirt to show internal equipment

Figure 14.3
Perspective view of the equipment of section 4

140 - Opening part of the skirt for maintenance and / or repairs
141 - Flue gas inlet in section 4
142 - Outlet of separate CO2 from section 4
143 - Outlet of 0 emission gas consisting of nitrogen and steam at the temperature of about 20° C
144 - Reacted collection tank for transfer to stripping
145 - Heat exchanger for matter stripping
146 - Lower sprinkler plant for reagent distribution
147 - CO2 stripping from the reacted liquid
148 - Upper sprinkler plant for reagent distribution

FIGURE 15
CO2 SEPARATION - MEMBRANE EQUIPMENT

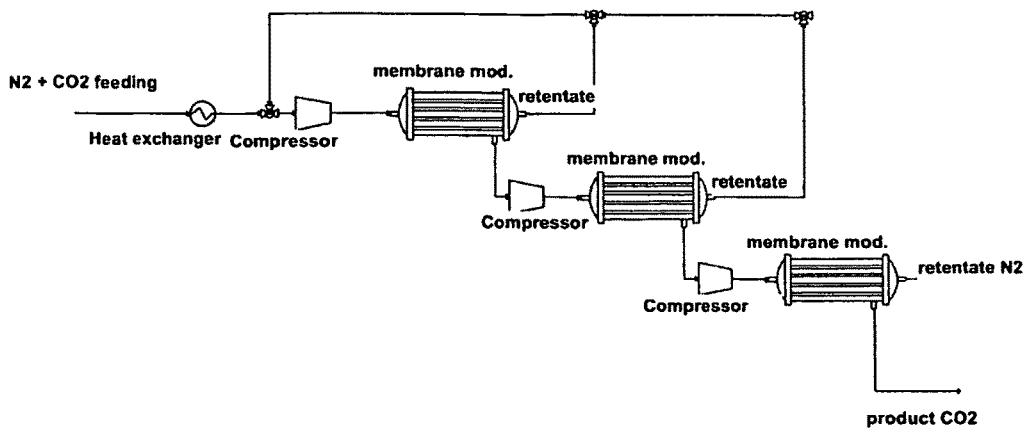

Figure 15
Diagram of the membrane equipment for separating CO2 from the flue gas released by sect. 3 of the reaction tower and that are input in section 4 of the tower when amines are used to separate CO2. If membrane modules are used for separation, the gas route is that of figure 15.1 wherein the flue gas represent the feeding (N2 + CO2) and the final part of the treatment is represented by the effluents of the third membrane module (3 passages of flue gases from membrane modules): CO2 and N2

FIGURE 16
HYDROGEN PRODUCTION BY THERMOCHEMICAL WATER SPLITTING

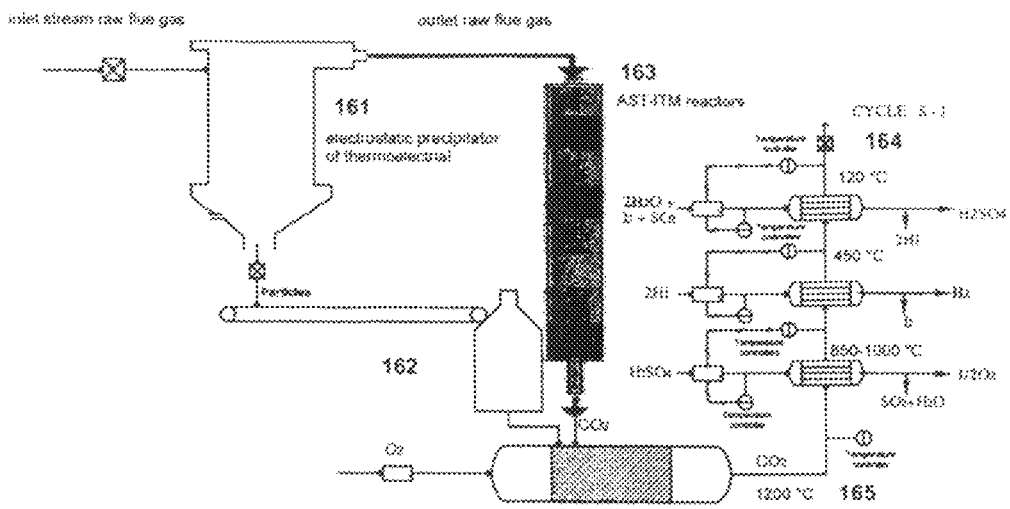

Figure 16.1 - Diagram of the AST plant for thermochemical water splitting

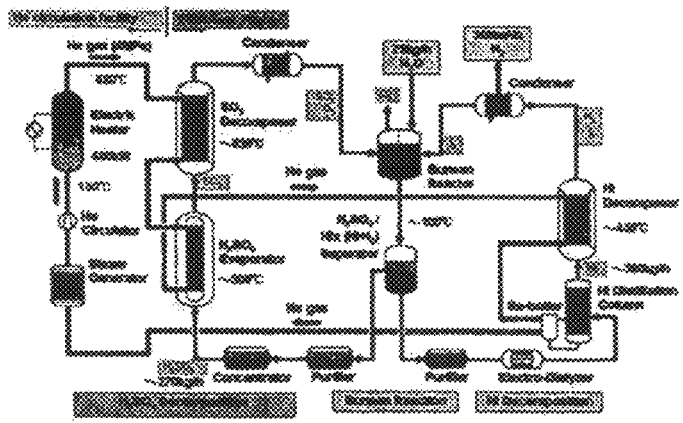

Figure 16.2 - Diagram of the JAEA plant (Japan Atomic Agency) for the thermochemical water splitting of the pilot plant for nuclear plant with sulphur-iodine cycle 161 - Electrostatic precipitator of thermoelectrical plant
162 - Furnace for burning unburnt coal particles
163 - AST plant for the supply of CO2 and O2 for the furnace
164 - Sulphur-iodine cycle AST plant modified for heat provided by coal dust thermoelectrical plant
165 - Exchanger

FIGURE 17
METHANOL PRODUCTION WITH MEMBRANE REACTORS

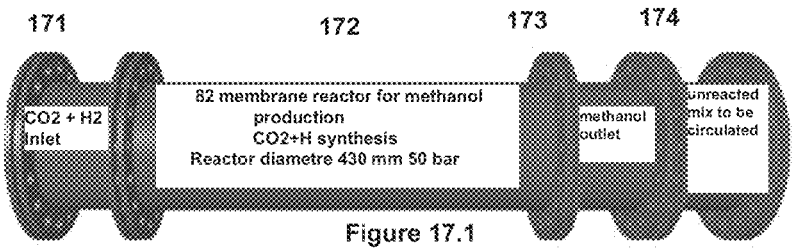

Figure 17.1

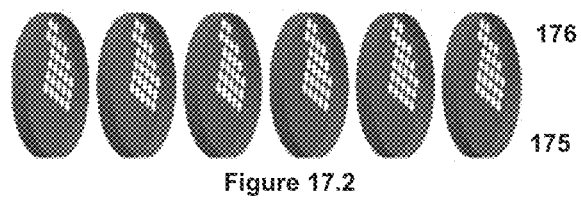

Figure 17.2

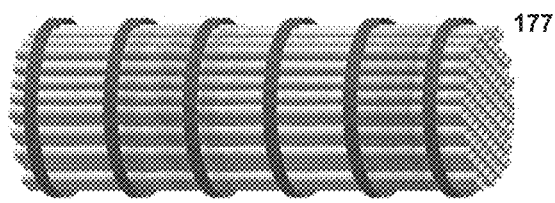

Figure 17.3

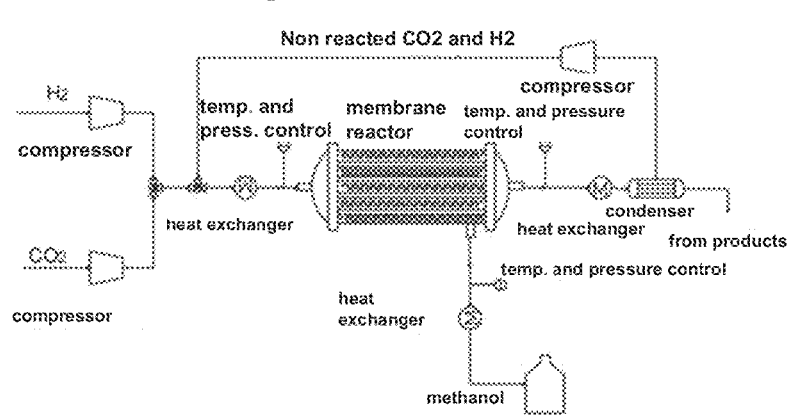

Figure 17.4

Figure 17.1 - AST reactor with an 82 membrane synthesis of methanol from CO2 + 3H2 at 50 bars
171 - H2 and CO2 mixing zone
172 - Membrane and catalyzer zone
173 - Methanol collection and delivery to storage
174 - Collection of non reacted and delivery to recirculation
Figure 17.2 - Set of spacing plates for membrane assembly and catalyst division
Figure 17.3 - Mounted tubular cylindrical membrane bundle
Figura 17.4 - Reactor diagram

FIGURE 18
Module with 12 towers for a supercritical coal dust thermoelectrical plant with power of 300 -:- 350 Mwel

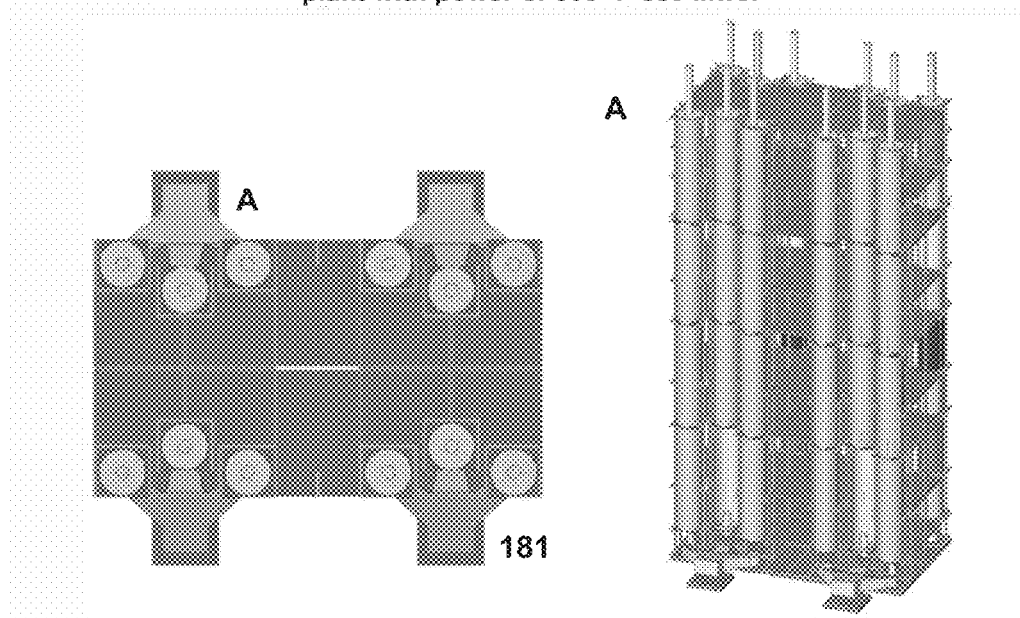

Figure 18.1
Layout. The module consists of 12 reaction towers connected to each other by the gas distribution system (181) of the plant. The plant has dimensions of 24.00 x 14.00 metres and has 8 storeys for a total surface of 1,700 m2.

Figure 18.2
Axonometry. The dead freight volume of the plant is about 12,000 m3 and can treat the flue gases produced by a thermoelectrical plant of 300 -:- 350 Mwel that represent the elementary modules of large power electrical plants.

FIGURE 19
Module with 60 towers for a supercritical coal dust thermoelectrical plant with a power of 1,320 Mwel

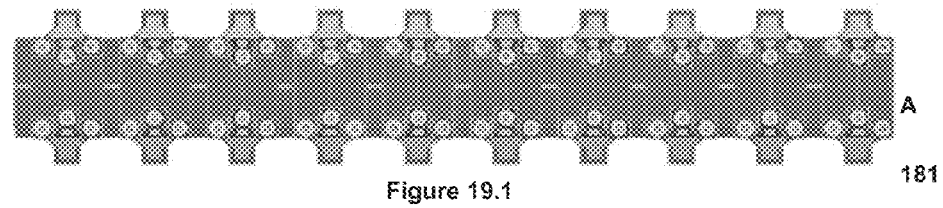

Figure 19.1      181

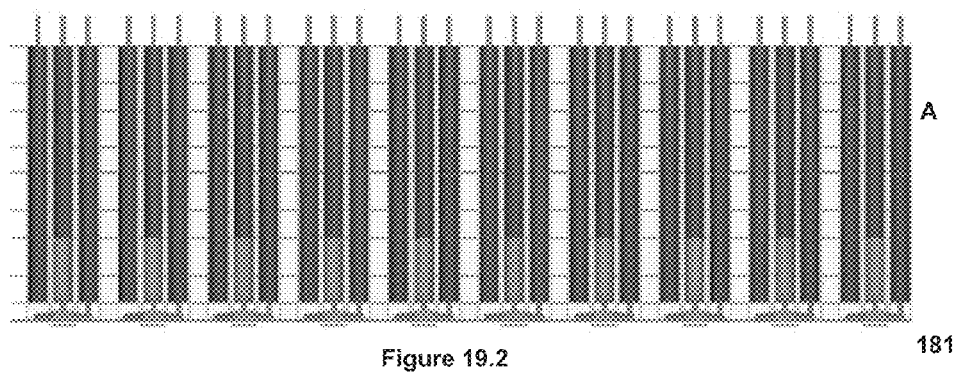

Figure 19.2      181

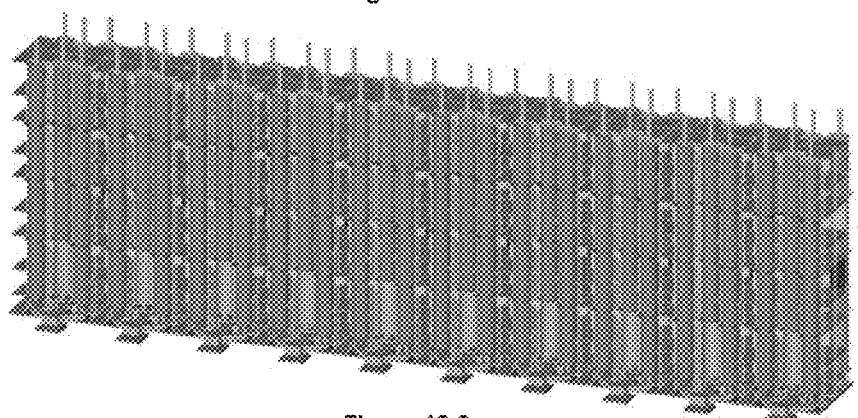

Figure 19.3

Figure 19.1: Plant: dimensions of 120.00 x 14.00 metres equal to 1,680 m2
Figure 19.2: Front: the plant develops on nine storeys for a volume of 62,000 m3
Figure 19.3: Perspective view: the plant treats 4,800,000 m3/h dry gas (scfm-dry) corresponding to the emissions of a supercritical coal dust thermoelectrical plant with a power of 1,320 MWe

MODULAR PLANT FOR REMOVAL OF POLLUTANTS FROM FLUE GASES PRODUCED BY INDUSTRIAL PROCESSES This application is a 35 U.S.C. §371 national phase of PCT/IT2008/000559 filed on Aug. 20, 2008, which claims priority to and the benefit of Italian Application No. RM2007A000446 filed on Aug. 20, 2007, the contents of which are incorporated herein by reference.

FIELD OF THE INVENTION

The present invention relates to a modular plant for removal of pollutants from flue gases produced by industrial processes.

In particular, the invention relates to a plant, constituting the so-called zero emission "AST-CNR/ITM system", the plant being equipped for smoke treatment, for separating and using the pollutants removed, for capturing $CO_2$ and transforming it into methanol in the membrane reactors comprised in the plant. This is composed of prefabricated modular elements with programmed and automatic operation, easy to mount and assemble on site without undergoing expensive plant stoppage.

PRIOR ART

It is known that industrial plants generate polluting substances that are subject to strict rules in relation to their release to the environment. To this end, industrial plants are provided with special devices/plants for the disposal/treatment thereof.

In the present description, reference is made to industrial flue gases from industrial processes and to the pollutants therein, as detailed hereinafter.

As may be easily understood, plants for the removal of pollutants from flue gases produced by industrial processes are essential to safeguard the environment. These are not modular, may be large sized, with consequent difficulties for assembly, transport, on site assembly and their need for repair and routing maintenance imply expensive and unavoidable stoppage of the production plants.

Moreover, there are no efficient plants that besides removing the pollutants are also equipped or set up for capturing $CO_2$ and for the use thereof. At present, $CO_2$ is not subject to subsequent transformation treatments, on the contrary it is preferably captured and pumped underground for permanent confinement thereof.

To the inventors' knowledge currently there are no plants for the complete removal of flue gases from industrial processes, including capture of $CO_2$, and transformation thereof into marketable secondary raw material. Moreover, current plants are not modular, nor easy to mount and assemble on site, nor they have limited size and moreover they require plant stoppage for maintenance and repair thereof.

SUMMARY OF THE INVENTION

A plant for the removal of pollutants from flue gases produced by industrial processes that overcomes the drawbacks mentioned above has now been made and is the object of the present invention. Said plant for the removal of pollutants is easy to be combined with any industrial plants that generate process flue gases and that hereinafter are generically referred to as "main plant". Especially advantageous is combining the modular plant of the invention with plants that operate burning fossil fuels.

The plant according to the present invention, along with the processes conducted therein, is described in the annexed claims and figures. Said plant is modular and comprises at least one vertical element A that hereinafter shall also be referred to as "reaction tower".

Preferably, the plant of the invention comprises a plurality of towers, optionally arranged in groups or units with 3 towers each.

Each reaction tower comprises at least one modular element, preferably a plurality of elements arranged vertically and described in detail hereinafter.

The modular elements shall also be referred with the term "sections" hereinafter. The main sections shall be intended for carrying out the following functions:

Removal of particulate matter (for example by electrostatic precipitators) with treatment and removal of chemical pollutants, such as heavy metals, chlorides, fluorides
Treatment and removal of SOx
Treatment and removal of NOx
Capture of $CO_2$
Production of hydrogen
Production of methanol The various sections may be combined according to the requirements of the plant and of the flue gases to be treated.

All of the above treatments are based on technical know-how known to the man skilled in the art which, in combination with the teachings of the description, allow easily carrying out the processes according to the present invention.

Further objects of the invention will appear more clearly from the detailed description of the invention.

BRIEF DESCRIPTION OF THE DRAWINGS

FIG. 2 shows a front view of the reaction tower A composed of sections 2.1 (particulate matter and metal treatment), 2.2 (desulphurisation) and 2.3 (denitrifying); and a perspective view of the main internal devices of which sections 2.1, 2.2 and 2.3 are provided with.

FIG. 3 shows block 1.2 of FIG. 1, which relates to the fourth section of the reaction tower. In particular, FIG. 3.1 shows the front views of the fourth section respectively with closed and partially open skirt; FIG. 3.2 shows the front view of the fourth section with closed skirt and the corresponding vertical section.

FIG. 4 shows block 1.3 of FIG. 1, which relates to hydrogen production. In particular, FIG. 4.1 shows an electrolyser SESPI; FIG. 4.2 shows an electrolyser Siemens Westinghouse; FIG. 4.3 shows a diagram of the production of hydrogen with thermochemical splitting of water.

FIG. 5 shows block 1.4 of FIG. 1, which relates to methanol production. In particular, FIG. 5.1 shows a thermo-electrical plant from whose flue gas the $CO_2$ is taken, which may be used for transformation into methanol; FIG. 5.2 shows a thermo-electrical plant wherefrom, using electrical energy it is possible to obtain $H_2$ to use for transforming $CO_2$ into methanol; FIG. 5.3 shows a membrane reactor that, starting from the reagents of FIGS. 5.1 and 5.2, carries out the catalytic transformation of $H_2$ and $CO_2$ into methanol; FIG. 5.4 shows the diagram of methanol production with membrane reactors.

FIG. 6 shows the reaction tower A in a series of possible configurations. In particular, FIG. 6.1 is a tower with four sections with flue gas inlet at 601 and flue gas outlet at 602; FIG. 6.2 shows a tower composed of sections 1° and 4'; FIG. 6.3 shows a tower composed of sections 1°, 2° and 3°; FIG. 6.4 shows a tower composed of sections 2° and 3°; FIG. 6.5 shows a tower composed of sections 3° and 4°.

FIG. 7 schematically shows the unitary plant module (shown in FIG. 6.1). In particular, FIG. 7.1 is the plan view, FIG. 7.2 is the front view, FIG. 7.3 is the perspective view of said unitary module, which can also act as pilot plant.

FIG. 8 schematically shows the bearing structure of the reaction towers, mounted on a support base, generally reinforced concrete 821 whereon the flue gas distribution plant is mounted, schematically shown in FIG. 8.1. The bearing structure is composed of erected frames 820 (FIG. 8.2), in this case, set up for housing three towers (not shown) and carries support surfaces 830 for the various tower sections (FIG. 8.2), which are shown into position in FIG. 8.4.

FIG. 9 shows the first section of the reaction tower A of the invention. In particular, FIG. 9.1 is a front view with closed skirt wherein there are indicated, from the bottom upwards, the tank zone, the mercury treatment zone, a first washing zone, the electrostatic precipitator zone, a second washing zone. FIG. 9.2 schematically shows a perspective view of the equipment contained in the first section. FIG. 9.3 shows a detail of the tube bundles of the electrostatic precipitator.

FIG. 10 schematically shows some details of the electrostatic precipitator zone of FIG. 9. In particular, FIG. 10.1 shows the electrode plant of the electrostatic precipitator; FIG. 10.2 shows a front view of the sprinkler plant; FIG. 10.3 shows a perspective view of the sprinkler plant of FIG. 10.2; FIG. 10.4 shows a top perspective view of the electrostatic precipitator zone with the tube bundles in position and closed skirt; FIG. 10.5 shows a perspective view, but relative to the view of FIG. 10.4, the skirt is open and one of the tube bundles is partly extracted (e.g. for repair requirements) for illustrating the modularity and the ease of removal of the elements that make up the plant of the invention.

FIG. 11 schematically shows some details of the mercury treatment zone of FIG. 9. In particular, FIG. 11.1 schematically shows a perspective view of the mercury treatment equipment; FIG. 11.2 is a perspective view of the tanks and of the reactor support surface; FIG. 11.3 is a perspective view of the ceramic cylinders of the reactor; FIG. 11.4 is a perspective view of the reactor with its own skirt, concentric to that of the electrostatic precipitator and spaced therefrom by the tank zone. Reference numeral 1151 denotes the sprinkler plant of the mercury reactor.

FIG. 12 shows the second section of the reaction tower A of the invention. In particular, FIG. 12.1 is a front view of the section with closed skirt; FIG. 12.2 shows a schematic perspective view of the equipment for the desulphurisation treatment wherein there are indicated, from the bottom upwards: the lower catalyst pack 1226, the lower sprinkler plant 1225, the median catalyst pack 1224, the median sprinkler plant 1223, the upper catalyst pack 1222, the upper sprinkler plant 1221. FIG. 12.3 shows the desulphurisation plant diagram.

FIG. 13 shows the third section of the reaction tower A of the invention. In particular, FIG. 13.1 is a front view of the section with closed skirt; FIG. 13.2 shows a schematic perspective view of the equipment for the denitrifying treatment wherein there are indicated, from the bottom upwards: a plurality of lower catalyst packs 1326, the lower sprinkler plant 1325, a plurality of median catalyst packs 1324, the median sprinkler plant 1323, the upper catalyst pack 1322, the upper sprinkler plant 1321.

FIG. 14 shows the fifth section of the reaction tower A of the invention wherein the $CO_2$ is separated by amine treatment. In particular, FIG. 14.1 shows a front view with closed skirt of the absorber reactor for capturing the $CO_2$, reference numeral 141 shows the flue gas inlet zone, reference numeral 142 shows the $CO_2$ outlet zone and reference numeral 143 shows the flue gas outlet zone (after the removal of the $CO_2$ the flue gas contains nitrogen and steam typically at a temperature of about 20° C.). FIG. 14.2 shows skirt 140 partially open for inspection/maintenance/repair. FIG. 14.3 shows a schematic perspective view of the equipment of the fourth section (144 storage tank of the reacted product to be transferred to stripping; 145 heat exchanger to carry out the reacted product stripping; 146 lower sprinkler plant for the reactive product distribution; 147 stripping of $CO_2$ from the liquid reacted product; 148 upper sprinkler plant for the reactive product distribution).

FIG. 15 shows the diagram of the membrane equipment for separating the $CO_2$ from the flue gas released by the third section of the reaction tower. When membrane modules are used for separation, the gas path is that shown in the diagram of FIG. 15, wherein the gas represents the supply ($N_2+CO_2$) and the final part of the treatment is represented by the effluents $CO_2$ and $N_2$. The membranes are arranged in a series and are located inside the section, shown in FIG. 3.2, overlapped to one another.

FIG. 16 schematically shows the hydrogen production. In particular, FIG. 16.1 shows the diagram according to the plant of the invention (161 electrostatic precipitator of the thermo-electrical plant; 162 furnace for burning unburnt coal particles; 163 plant section illustrated in FIG. 15 for the supply of $CO_2$ and $O_2$ for the furnace; 164 modified sulphur-iodine cycle plant for using the heat provided by the coal dust thermo-electrical plant). FIG. 16.2 plant diagram known as JAEA for the thermo-chemical splitting of water of the pilot plant for nuclear plant with sulphur-iodine cycle. FIG. 17 shows the production of methanol with membrane reactors. In particular, FIG. 17.1 is the front view of a closed reactor with 82 membranes (reactor diameter, typically 430 mm and pressure 50 bar) (171 $H_2$ and $CO_2$ mixing zone; 172 membrane and catalyst zone; 173 methanol collection zone for delivery to storage; 174 non-reacted product collection zone and delivery to recirculation). FIG. 17.2 shows a schematic perspective view of a plurality of spacer plates 175 required to assemble the membranes (through holes 176 are visible). FIG. 17.3 is a schematic perspective view of a bundle of assembled cylindrical membranes 177. FIG. 17.4 shows a diagram of the reactor of FIG. 17.1.

FIG. 18 schematically shows a plan (FIG. 18.1) and perspective (FIG. 18.2) view of a 12 tower module for a supercritical coal dust thermo-electrical plant with a power of 300-:-350 MWel. The layout of FIG. 18.1 shows a module with 12 reaction towers connected to each other by the flue gas distribution system 181; the layout has a size of 24.00× 14.00 m and has 18 storeys for a total of 1700 m² surface. FIG. 18.2 shows an axonometric view, the volume, dead freight, of the plant is about 12000 m³ and is capable of treating the flue gas produced by a high power thermo-electrical plant. Reference numeral 181 indicates the flue gas distribution system which, captured by the gas duct of the thermo-electrical plant by a fan, is distributed for treatment to the towers, through motor driven gates controlled by the plant general control. The volume of dry smoke treated by the module is typically comprised respectively between 1.1 and 1.3 million m³/h.

FIG. 19 schematically shows a 60 tower module for a supercritical coal dust thermo-electrical plant with a power of 1320 MWel. In particular, FIG. 19.1 is a plan view sized 120.00×14.00 m equal to 1680 m². FIG. 19.2 shows a perspective view. The plant develops on nine storeys for a volume of 62000 m³. FIG. 19.3 shows a perspective view. The plant may be sized to treat 4,800,000 m³/h dry smoke (scimdry).

DETAILED DESCRIPTION OF THE FIGURES

Figure 1:
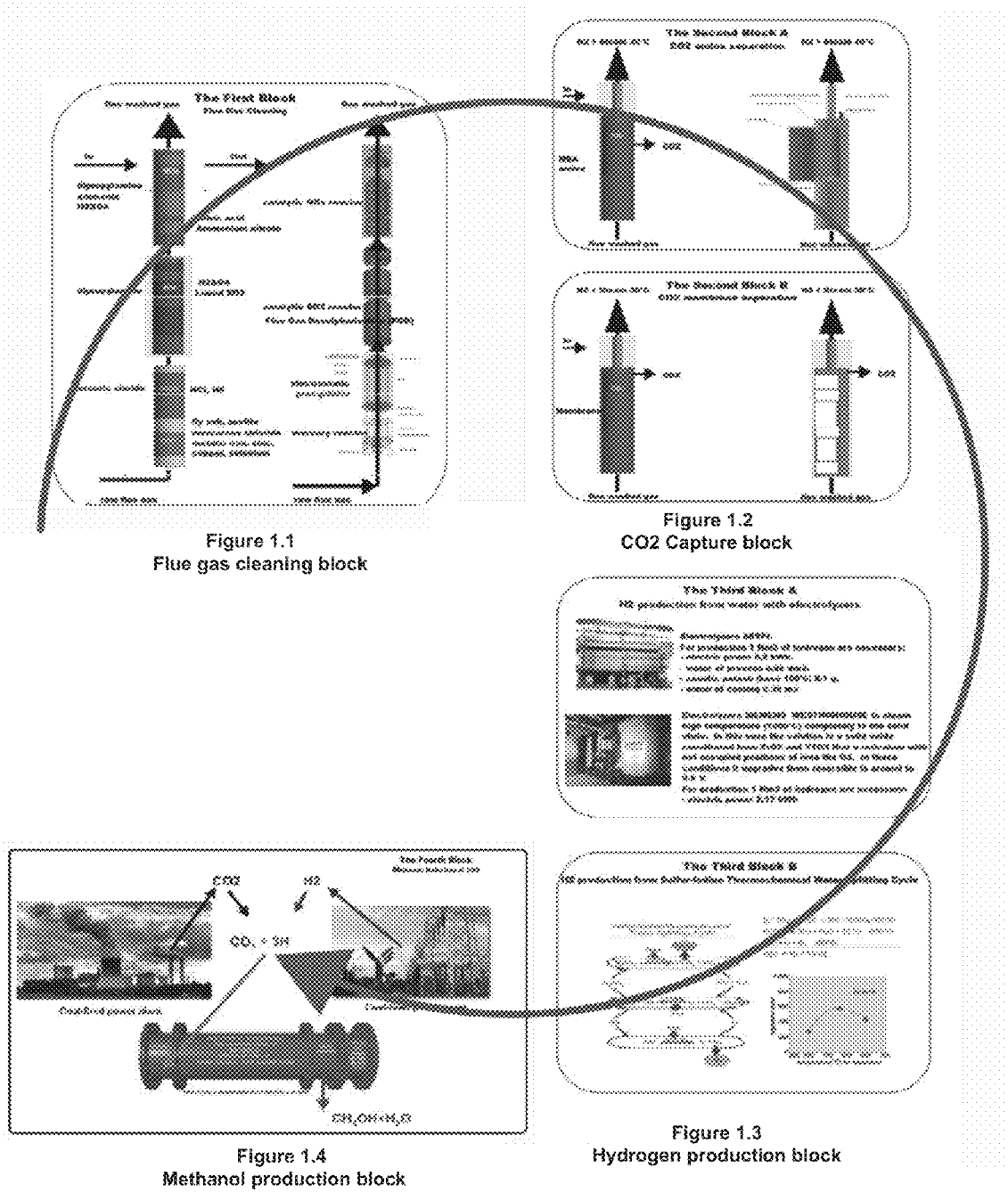
FIG. 1 shows the block diagram of FIG. 1 and schematically shows blocks: 1.1-flue gas cleaning; 1.2-capture $CO_2$; 1.3-hydrogen production; 1.4-methanol production.
Figure 1A:
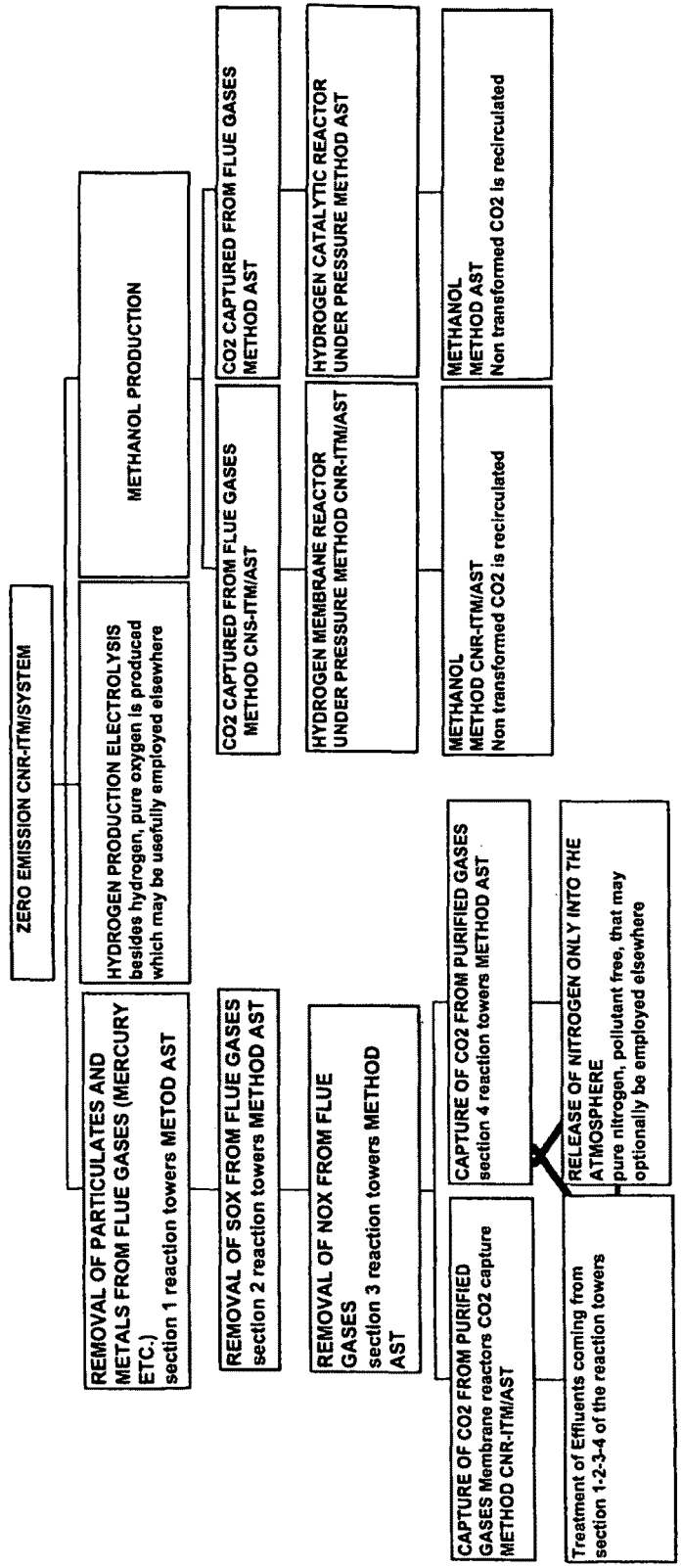
FIG. 1A shows the block diagram of the "ZERO EMISSION AST-CNR/ITM SYSTEM".

FIG. 1A shows the block diagram of the "ZERO EMISSION AST-CNR/ITM SYSTEM" constructed for being connected to a coal dust thermo-electrical plant (main plant), but it may be easily adapted by the man skilled in the art according to the following instructions to other industrial plants that operate using fossil fuels.

The diagram in FIG. 1 consists of blocks 1.1, 1.2 1.3 and 1.4, that show the fundamental treatment steps and the basic plant elements that starting from the flue gas coming from the main plant, lead to the production of methanol using only what is produced in the plant in terms and in the form of production waste, which would otherwise be disposed of, with considerable increase in terms of management of the main plant, especially because most of the times it is disposal of special and highly pollutant waste.

Figure 2:
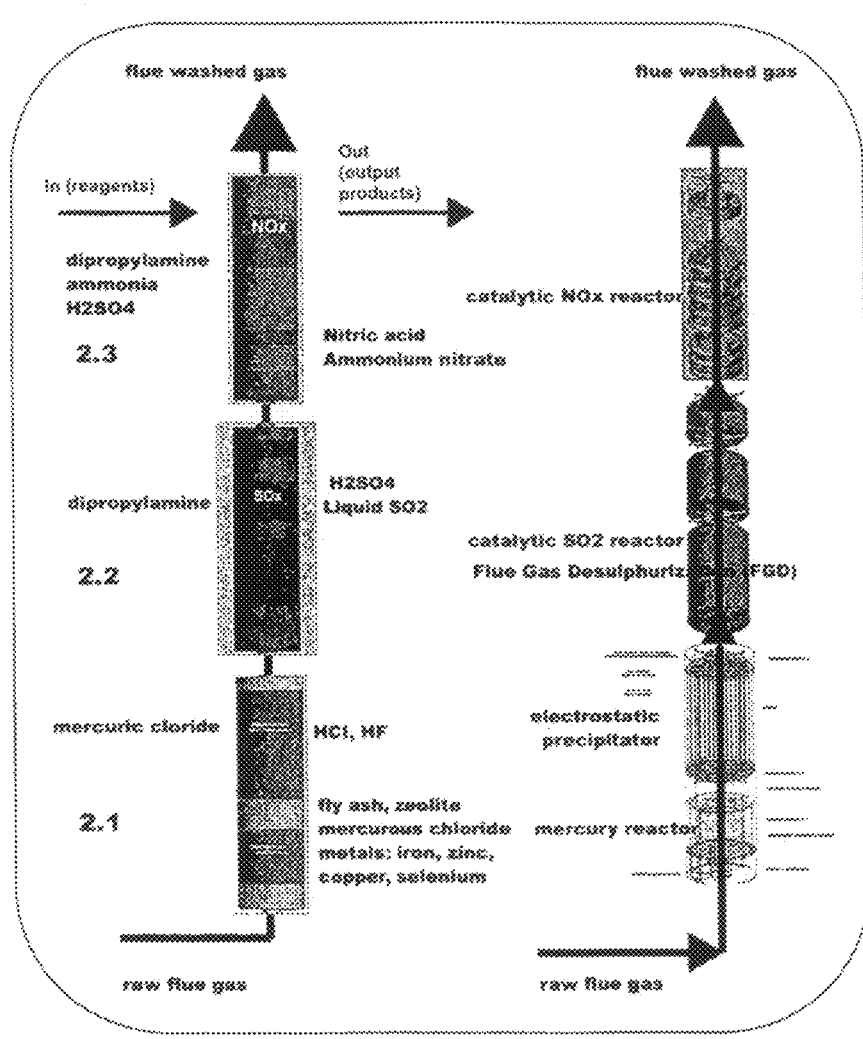
FIG. 2 shows block 1.1 of FIG. 1, which schematically shows the first three sections of the reaction tower of the vertical element A. In particular.

FIG. 2 shows block 1.1 of FIG. 1, that schematically shows the first three sections of the reaction tower of the vertical element A, wherein there are conveyed the raw flue gas coming from the boiler of the electrostatic precipitator of the thermo-electrical plant, located upstream of the modular plant of the invention. Said gas is conveyed to a duct that axially crosses the various sections of the tower to be treated in the following sequence:
- section 2.1: here, a washing stage is performed for removing heavy metals, fine particles (<100 micrometres), halogenides in general, chlorides and fluorides in particular, heavy metals, optionally mercury;
- section 2.2: the desulphurisation treatments are carried out here, in particular desulphurisation with the use of amines (e.g. dipropylamine);
- section 2.3: the denitrifying treatments are carried out here, in particular denitrifying with the use of dipropylamine, ammonia and sulphuric acid.

FIG. 3 shows block 1.2 of FIG. 1, which relates to the fourth section of the reaction tower, where there occurs the separation between $CO_2$ and the nitrogen contained in the already washed flue gas coming from the previous section. The separation may typically occur with different methods, which implies different setup of the sections:
- the section of FIG. 3.1 performs the separation of $CO_2$ from the amines treated by stripping;
- the section of FIG. 3.2 performs the separation of $CO_2$ from the amines using the membrane technology;

At the end of the separation process, the amines are returned to circulation and $CO_2$ is delivered to subsequent treatments.

FIG. 4 shows block 1.3 of FIG. 1, wherein there are shown the means used by the AST-CNR/ITM system for carrying out the hydrogen production, required for the methanol synthesis starting from $H_2$ and $CO_2$. With reference to a thermo-electrical plant with a power of 1320 MW, a suitably sized electrolyser plant will be required (an amount of hydrogen equal to 161 ton/h is required for the complete transformation of the $CO_2$ produced by the combustion of coal –600.00 Nm³/h). Electrolysers that may be used may be of the following type:
- electrolysers at room temperature, that require the higher amount of electrical energy per Nm³ of hydrogen produced. FIG. 4.1 shows a SESPI electrolyser that can operate with the following operating data (the data below refer to the general case, specific and more detailed data may be provided in relation to particular operating conditions of the plant and locations, or for installations integrated with other customer's plants). The following is required for the production of 1 Nm³ pure hydrogen:
   Electric energy 5.8 kWh
   Process water 0.85 dm³
   Caustic potash (base 100%) 0.1 g
   Cooling water 0.35 m³ (source SESPI)
- high temperature electrolysers (typically around 1000° C.) and with solid electrolyte (usually a mixture of $ZrO_2$ and $Y_2O_3$), that require a lower amount of electric energy per Nm³ hydrogen produced (about 2.17 kW/h with reduction of electric energy by about 37%) (FIG. 4.2 shows an electrolyser Siemens Westinghouse);
- high temperature electrolysers cooled by gas of the type HTGR (High Temperature Gas Reactor) (diagram of FIG. 4.3) used for the thermochemical splitting of water by Japan Atomic Energy Agency (JAEA) for producing hydrogen by the process called S—I Sulphur-Iodine. This is the most advantageous method in terms of energy, because only the thermal energy generated during the electric energy production processes of the main plant is used to produce hydrogen.

It should be noted that hydrogen production in a thermo-electrical plant takes place using also the sulphuric acid produced by the desulphurisation of the gas and whose contribution, in terms of hydrogen produced, is about 0.55% of the overall requirement per each percentage point of sulphur contained in the fossil fuel or coal. This stage is carried out in an additional plant section with iron dust, as described below.

FIG. 5 shows block 1.4 of FIG. 1, wherein there are shown the means used by the AST-CNR/ITM system for carrying out the methanol production. In particular, FIG. 5.4 schematically shows the methanol production diagram that uses membrane reactors to conduct the catalysis between $H_2$ and $CO_2$ for producing methanol.

FIG. 6 shows various types of setups, according to the type of main plant the modular plant of the invention shall be connected to. Note that each section may be separated from the others to which it is connected to and is constructed so as to be inspectable and/or repairable separately. In particular, FIG. 6.1 schematically shows a first embodiment of a reaction tower A divided into four sections, three for removing the pollutants: the first at the bottom, for particulate matter and metals, the second for SOx (desulphurisation or deSOx) and the third for NOx (denitrifying or deNOx) and finally, the fourth, on top, for $CO_2$ capture. All the sections, and thereby all the tower, are prefabricated, can be made in workshop, assembled and fitted with all the utilities, wired and tested at the workshop, prior to transport on site for their erection.

The tower is provided with a central main duct that crosses it axially, wherein the gas flows and entering from the bottom in 601 they cross each of the sections to be treated therein, and come out from the top in 602 after washing and separation from $CO_2$. Each section is provided with inlet and outlet ducts (not shown) for the inlet of reagents and the outlet of the effluents to be treated in complementary plants (not shown) with outlet of, the end products (as shown in FIG. 2). Each section is connected to the previous one and to the next one by opening and sealed connecting means.

Each of FIGS. 6.2, 6.3, 6.4 and 6.5 shows further embodiments of tower A based on different ways of combining the different pollutant removal sections (from the first to the fourth), thus realising different reaction towers suitable for the different requirements of production plants. In particular, FIG. 6.2 indicates the tower composed of sections 1° and 4° (metal removal and $CO_2$ separation); FIG. 6.3 indicates the tower composed of sections 1°, 2° and 3° (metal removal, deSOx and deNOx); FIG. 6.4 indicates the tower composed of sections 2° and 3° (deSOx and deNOx); FIG. 6.5 indicates the tower composed of sections 3° and 4° (deNOx and $CO_2$ separation).

Such interchangeability of setup of the reaction towers allows using the plant of the invention as retrofit for any main plant, also allowing a reduction in investment costs. That is, the plant of the invention is adaptable to any other already existing plant, as it can be perfectly integrated with pre-existing structures in plants that require being upgraded/improved/modified to adjust to increasingly stricter anti-pollution standards.

FIG. 7 schematically shows the unitary plant module in plan view (FIG. 7.1), front view (FIG. 7.2) and in perspective (FIG. 7.3). The unit module may also have the function of a pilot plant in scale 1:1 for the tests to be carried out in the plants to be reclaimed.

FIG. 8 shows the assembly diagram of the reaction towers. Like the reaction towers, also the bearing structure is prefabricated at the workshop and can be assembled on site. FIG. 8.1 shows the flue gas distribution plant diagram, inserted at the base of the bearing structure. FIG. 8.2 shows the erection of the bearing structure of the three tower module, made with broad flanged beams 820 on the support base 821; FIG. 8.3 shows the assembly of the prefabricated floors 830 and FIG. 8.4 shows the assembly in this case of three reaction towers A.

The combustion gas (flue gas) withdrawn at the outlet of the main electrostatic precipitator, for example of a thermo-electrical plant (not shown) or at the outlet of the bag dust removers (not shown), is conveyed by a duct (not shown) to the zone where it is distributed to the reaction towers. There is one distribution zone every three towers. In this part of the plant (FIG. 8.1), and before it is introduced into the reaction towers, flue gas typically has a temperature of about 170° C. It is first made to pass through a heat exchanger (not shown) where it releases a part of its heat and, at the temperature of about 30° C., it is introduced in an electrostatic precipitator where the settle of particulates particles, then are collected and sent to selection in special treatment and selection tanks. At this stage, the flue gas, through a three-way distribution line, is addressed and introduced into the reaction towers, by the opening of motor-driven gates controlled by software that opens said gates according to the amount of incoming gas. For gas flow rates below the sum of what can be processed in the 3 towers, the system will close 1 or 2 gates. In each flue gas duct (they are generally two as the towers are usually arranged on two facing rows, as per FIGS. 18 and 19) at the height of the branching that sends the gas to the groups of 3 reaction towers and at the beginning of the service duct for the 3 towers, there is another motor-driven gate for starting up or excluding the group of three towers. Opening or closing the gas distribution towers is controlled by software, which automatically opens the inlet gates to the groups of 3 towers based on the amount of gas produced in the plant and sensed by the various sensors placed in the duct. This is better illustrated in FIGS. 18 and 19 (plant with 12 and 60 towers respectively, organised by threes in two facing rows).

FIG. 9 shows in FIG. 9.1 the front of the first section of the reaction tower. Such section has a substantially cylindrical shape, preferably with diameter of 2400 mm and height of 8500 mm and is sized for withstanding a pressure of 5 bars. It comprises a device for the treatment of mercury and heavy metals and a device for the electrostatic removal of fine particulates (ESP). Some details of the tube bundles of the electrostatic precipitator are shown in perspective respectively in FIG. 9.2 and in FIG. 9.3, as follows: 920 the skirt; 931 the first tube bundle; 932 the second tube bundle; 933 the support of the first electrode plant; 934 the support of the second electrode plant; 935 the first electrode plant; 936 the second electrode plant; 937 the electrodes; 938 the particulates collection tubes.

FIG. 10 shows further construction details of section 1 of the reaction tower.

FIG. 10.1 shows the AST electrode plant with the system for locking the electrodes to the tube bundle and with the electrical supply system.

When one or both the component elements of the tube bundle are removed, the respective electrode systems are removed therealong, which are fixed to the tube bundle so as to prevent the same electrodes from moving and colliding against the alveolar walls, thus causing damages to the plant.

Safety measure: the movement or release of an electrode automatically causes the interruption of the current flow to the electrodes to prevent possible damages to the plant. The same happens prior to opening the tube bundle washing system.

FIGS. 10.2 and 10.3 respectively show a plan view and a perspective view of the sprinkler plants of the section. In this case, the washing is carried out by 38 sprinklers.

The washing water is collected in the storage tank formed in the lower portion of the section and whose vertical walls consist of the skirt and of the flue gas inlet duct, whereas the bottom consists of the bottom of the section. It is open at the top and the washing water gathers therein by fall. An umbrella prevents the washing water from falling into the gas duct and further ensures a turbulent motion to the gas to ensure a better contact between the flue gas and the washing water. Floats and pressure sensors prevent the washing water from overflowing into the flue gas duct, starting recirculation (not indicated in the Figure) or start up pumps for the complementary plants (not indicated in the Figure) for the effluent treatment. The tank capacity typically is about 2.50 $m^3$.

The construction and use features of the sections of the AST reaction towers are shown in FIGS. 10.4 and 10.5 and are indicative of the system modularity.

This device allows operations for repairing and maintaining the sections without needing to disassemble the entire reaction tower. In fact, the sections may be opened for carrying out facilitated operations of assembly, inspection, repair, and maintenance, as is shown in the figure.

For the operations to be carried out in the first section, it is possible to open the external wall 920 (skirt) of the section to extract the whole tube bundle or only a part thereof, it being divided into two elements (931 and 932), specularly symmetrical. Once one element 931 has been removed it is possible to access the entire reaction tower to proceed to the required repairs.

FIG. 10.4 shows the WESP AST in a perspective top view, with the alveolar tube bundle already equipped with the electrode plant.

FIG. 11 shows, again for the same section 1°, the reactor for the removal of mercury. The figure schematically shows an AST reactor, both in transparent axonometry of the entire first section (FIG. 11.1) and only of the part relating to the mercury removal reactor (FIG. 11.2), placed inside the first section and used also for removing other metals contained in the flue gas. The flue gas that enters the AST reaction tower, passing inside this reactor, undergoes the Boliden Norzink removal process for removing mercury from the gas.

A solution of mercuric chloride containing $HgCl_2$ is circulated in a tower consisting of a plurality of concentric porous ceramic rings (FIG. 11.4) soaked in mercuric chloride. The process flue gases which contain the mercury pass through the gas inlet duct and longitudinally cross the ceramic ring tower (FIG. 11.4) and here, the mercury contained in the gases reacts with the mercuric chloride to produce mercurous chloride. The mercurous chloride is insoluble and precipitates in the container of the solution arranged at the bottom of the reactor. The flue gas flow circulates inside the ceramic ring tower, crosses them and leaves the reactor through the side holes that carry the gas flow to the remainder of the section.

The clarified solution contained in the tank overflows into the next tank side by side, where the concentration of mercurous chloride is lower, more mercurous chloride is added and such solution is pumped to the reagent ceramic tower to start the cycle.

The solids that collect onto the bottom of the tank/primary decanter flow to the secondary decanter. In the decanter, zinc powder can be added to promote precipitation of the mercury from the solution. The solids of the secondary decanter are discharged in deposits (not shown) from which they are sent either for sale or to other manufacturing. All the operations are programmed and automated. Liquids are handled by pumps and the solids are discharged by hoppers with motor driven opening and discharge.

FIG. 12 schematically shows the front view (FIG. 12.1) of the second section of the AST-CNR/ITM reaction tower for SOx treatment. The $SO_2$ contained in the flue gas is adsorbed on an absorbent which is then regenerated, releasing liquid $SO_2$, or sulphuric acid ($H_2SO_4$) or finally, pure sulphur.

The schematic perspective view of FIG. 12.2 shows the absorbing elements 1222, 1224, and 1226 that make up the second section of the AST-CNR/ITM reaction tower for the SOx removal. Solid supports are contained therein which are drizzled with water containing amine, typically dipropylamine (DPA), with the sprinkler devices 1221, 1223 and 1225, placed on top of the trays.

The flue gas coming from the first section, after undergoing an adiabatic process and the saturation in $H_2O$ of the gaseous current, is subject to the particulates precipitation with wet electrofilters (tube bundles). This treatment (not present in traditional plants) is used in the AST-CNR/ITM system to ensure that the conversion processes for the production of $SO_2$ are not negatively affected by the presence of powders that could impair the catalyst activity. The ancillary plants in this section comprise a reactor and a filter/press for realising a neutralisation stage with limestone of the bleed extracted from the circulation. FIG. 12.3 shows the operating diagram of the elements of FIG. 12.2.

FIG. 13 schematically shows the third section of the reaction tower AST-CNR/ITM designed for denitrifying. FIG. 13.1 is the schematic front view of the third section for denitrifying of the flue gas in the reaction towers AST-CNR/ITM. There are shown the cylindrical annular tanks 1322, 1324 and 1326 of the catalysts, the sprinkler devices 1321, 1323 and 1325 and the effluent storage tank, also shown in the bottom part of the section. The flue gas is fed to the section through the central duct 1310, and passing through the tanks, it is placed in contact with the liquids sprayed by the sprinklers.

The AST process exhibits innovative features in gas denitrifying as compared to traditional processes (SCR), as it is based on the overall reaction $$NO+NO_2+2NH_3+H_2O+O_2=2NH_4NO_3 \quad (3)$$

result of the two partial reactions $$NO+NO_2+2NH_3+H_2O=2NH_4NO_2 \quad (1)$$

$$2NH_4NO_2+O_2=2NH_4NO_3 \quad (2)$$

wherefrom it is understood that in order to realise the stoichiometry of the reaction (3) it is necessary to have a molar ratio $NO/NO_2$ equal to 1, which is very far from the conditions of incoming gas (generally a ratio equal to 10-:-20). A device is used to obtain the equimolar ratio: a share of the solution circulating in the NOx section is sent, in the ancillary plants and complementary to the reaction tower, to a reactor (RA1) (not shown) wherein the ammonium nitrate is dissolved with $H_2SO_4$ and in suitable temperature and pressure conditions it is converted into $NO_2$. The nitrogen oxide gas by about 50% is recombined into the current of flue gas coming out of the SOx section to adjust the $NO/NO_2$ ratio to values close to the unit and the balance $NO_2$ is sent to the complementary unit HNE (not shown) wherein the conversion into $HNO_3$ takes place, along with the subsequent absorption for the production of solutions of commercial nitric acid (65%). In short, a circulation of $NO_2$ is set between the NOx tower and the complementary reactor RA1, which is the process core.

The reagent circulating into the sprinkler plants of the section is a $NH_3$ solution.

The non reacted part (about 10%) of SOx is removed in the first part of the section.

The novelty and the advantages of the system are shown by their operation at low temperature, about 25° C. compared to 300° C.-:-450° C. of the traditional SCR processes, which among the other things are subject to the "ammonia slip" phenomenon, that is, to the discharge of ammonia into the flue gases, when there is an excess of reagent compared to the $NO_2$ contained in the gas and which, together with the excess of $SO_2$ in the flue gases causes the breathing difficulties that occur close to plants of this kind. Moreover, in this way there is the further advantage of reducing the $SO_2$ emissions to a value of 5 mg/Nm$^3$, compared to the traditional plants that barely reach 300 mg/Nm$^3$.

The schematic axonometric view of the third section is shown in FIG. 13.2

FIG. 14 is a schematic front view of the fourth section of the reaction tower AST-CNR/ITM designed for $CO_2$ capture.

This section is designed for absorbing and capturing the $CO_2$ by amine compounds kept in solution with water and sprayed by sprinkler plants 146 and 148 on the flue gas coming from the previous section and fed to the fourth section through the central inlet duct 141.

The amines in contact with the flue gas capture the $CO_2$ and modify the values of concentration of the solution that is conveyed and collected in the bottom tank 144. Tank 144 is formed in the lower portion of the section and whose vertical walls consist of skirt 140 and of the flue gas inlet duct 141, whereas the bottom consists of the bottom of the section. It is open at the top and the amine solution gathers therein by fall. An umbrella prevents the amine solution from falling into the gas duct and further ensures a turbulent motion to the gas to ensure a better contact between the flue gas and the solution. Floats and pressure sensors prevent the solution from overflowing into the flue gas duct, starting the pumps (not shown in the Figure) that bring the solution rich in $CO_2$ into the stripping tower. The tank capacity typically is about 1.750 m$^3$.

In the stripping tower, the amine liquid is heated by the coil heat exchanger 145 with vapour supplied by complementary equipment (not shown) releasing the $CO_2$, previously absorbed, which is removed by duct 142, and regenerating the adsorption solution that is transferred by pumps to the complementary plant tank (not shown) for feeding of the plants. The $CO_2$ is collected in special tanks for further use.

FIG. 15 is the simplified diagram of a $CO_2$ separation unit with membrane equipment.

This membrane solution is an alternative to the separation described previously in FIG. 14 of the fourth section of the AST reaction towers (which takes place with the amines) and is a novelty and peculiarity of the AST-CNR/ITM system.

A gaseous current (flue gas) is taken into consideration with a flow of 4600000 Nm³/h, and is basically made up of nitrogen, watery vapour and carbon dioxide since, in the treatments previously described the pollutants were removed in the following concentrations:

$CO_2$: 14%

$N_2$: 86%

Starting from the above gaseous rate, the aim is to obtain a gaseous current rich in $CO_2$ by the use of membranes.

Some types of ceramic and polymeric membranes are taken into account below and a computation code was used to predict the level of separation of carbon dioxide based on the important design parameters such as the stage cut, the pressure ratio and the required membrane surface.

If membrane modules are used for separation, the flue gas path is that of FIG. 15, wherein the gas represents the supply ($N_2$+$CO_2$) and the final part of the treatment is represented by the effluents of the third membrane module (3 passages of gas into the membrane modules): $CO_2$ and $N_2$.

$CO_2$ is sent to the storage zone prior to its use, after having undergone a compression process that will raise the $CO_2$ pressure to 50 bars. The process, described hereinafter, is an innovative process and to the inventors' knowledge there are no other plants that use the membrane thus used for separating the $CO_2$ from the flue gas.

FIG. 16 shows the diagram of the AST plant for the hydrogen production through the thermochemical splitting of water. This hydrogen production method by means of HTR reactors (High Temperature Reactor) was first studied by the DOE (Department of Energy) ordered in the Seventies to the General Atomics, Sandia National Laboratories, and to the University of Kentucky which identified as many as 115 possible processes.

Only 2 of them were found interesting: UT3 (by the University of Tokyo-3), based on cycle Ca—Br—Fe, and I—S.

With this type of reactor (HTR) it is possible to produce hydrogen thermochemically, too. In fact, one of the methods for decomposing water is to administer heat at a high temperature, in the range of 3000° C. (pyrolysis). However, this implies serious technological difficulties, especially as regards the selection of the most suitable materials for operating at those temperatures.

The alternative was to use an appropriate thermo-chemical cycle to obtain the splitting of water, thus converting the heat supplied into chemical energy (with a given yield function of the selected cycle and of the machinery that performs it).

The studies involved the major centres of atomic research and among these, the one that received excellent results was the JAEA (Japan Atomic Energy Agency) which presented its pilot plant for an HTR that uses the cycle I—S and whose diagram is that shown in FIG. 16.2. The presentation took place with the publication of an article in the "Journal of NUCLEAR SCIENCE and TECHNOLOGY, Vol. 44. No 3, p. 477-482 (March 2007).

The best yields (up to 52%) and the nature of chemical reactions involved (all at the fluid state, unlike UT3) led to prefer the latter.

In such process, the only reagent used is water, which is splitted into 3 stages by heat, providing oxygen and hydrogen; all the other reagents are fully recycled (thereby without generating harmful effluents for the environment). The reaction diagram of the cycle is as follows

| | |
|---|---|
| $H_2SO_4 \rightarrow SO_2 + H_2O + \frac{1}{2}O_2$ | (850° C.) |
| $I_2 + SO_2 + 2H_2O \rightarrow 2HI + H_2SO_4$ | (120° C.) |
| $2HI \rightarrow I_2 + H_2$ | (450° C.) |
| $H_2O \rightarrow H_2 + \frac{1}{2}O_2$ | | and it is divided into three main steps:

the thermochemical splitting of sulphuric acid (at the temperature of about 800° C.) into sulphurous anhydride, water and oxygen (process by-product);

the (exothermic) reaction of iodine with the sulphurous anhydride, produced by the sulphuric acid, and with water (used in the process) with formation of new sulphuric acid (put back into circulation) and hydroiodic acid (at the temperature of about 120° C.); such reaction is called Bunsen reaction;

thermochemical splitting of the hydroiodic acid (at the temperature of about 450° C.) with formation of iodine (put back into circulation) and hydrogen;

Process by-product (besides oxygen) is the heat at the temperature of about 100° C., in turn usable for other applications (for example, remote heating).

This has allowed AST to design a further way to intervene on the efficiency of the thermo-electrical plant the modular plant is associated to, since a part of the heat of the plant is recovered to be used for the production of hydrogen by chemical thermolysis of water according to the diagram of FIGS. 4.3 and 16.1.

It is thus possible to recover in the general electrostatic precipitator 161, the part of unburnt coal of the plant, which can be assessed as about 6%-:-10% of the coal fed to the boiler, and contained in the plant volatile ashes, the recovered coal is burnt in an atmosphere rich in $O_2$, also present at the plant for the production of hydrogen by electrolysis (162).

This last operation allows obtaining ashes free from unburnt coal which are generally sent for marketing as pozzolana cement, but that in this way can advantageously be mixed to clinker cement (any presence of unburnt coal in the cement not treated in this way would cause zones of discontinuity of resistance in the cement concrete casts or in the mortars. This makes the volatile ashes not sellable and thus they must be sent to special dumps; (Official Gazette n. 108 of Oct. 5, 2002), coal ashes are identified by code CER 10 01 02 and classified as special non hazardous waste). In this way, large amounts of materials are recovered and all of the ashes produced by the plant. Considering that a thermo-electrical plant of 1320 MWel burns 3,500,000 tons coal in one year, the ashes produced sum up to about 15%, every year the thermo-electrical plant therefore produces 525,000 tons ashes that can all be sent for sale, greatly improving the central profitability.

In 164 there is shown the Sulphur-Iodine cycle, modified with the exchanger 165, for allowing the execution in a thermo-electrical plant.

A further difference made by AST was to replace helium gas with $CO_2$ (present in the AST system 163) in the high temperature ceramic exchanger 165 for the cycle S—I.

FIG. 17. Schematic view of a reactor with 82 membranes AST-CNR/ITM for the production of methanol from the synthesis of $CO_2$ and $H_2$. The reactor was designed by AST-CNR/ITM and it is shown in FIG. 17.1.

FIG. 17.3 shows the perspective view of the pack of 82 ceramic membranes of the AST-CNR/ITM reactor for methanol production and FIG. 17.2 is the view of the trays required for aligning the membranes and equally distributing and keeping on site the catalyst.

The membrane bundle, kept together by 6 spacing plates, globally shows the base module for the ceramic membrane reactors AST-CNR/ITM.

FIG. 17.4 shows the operating diagram of the reactor. Calculations and drawings are valid and confirmed; they are based on laboratory experience. The operating pressure was brought to 50 bars and thereby, the membrane reactor was designed in detail, which has an inner diameter of 400 mm and with 82 membranes having the inner diameter of 20 mm with catalyst outside the membrane.

The reactor at 50 bars produces 1230 kg/h methanol circulating 1158 m³/h $CO_2$ and 3500 m³/h $H_2$ (with excess of $H_2$).

The overall outlet gap of the 82 membranes is m² 0.02575, so the methanol outflow speed is:

$$V = 1230/0.02575/3600 = 13.27 \text{ m/s}$$

An outflow tube for the methanol is thus required which starts from the second section with 200 mm diameter, in any case typically suitable for preventing excessive turbulence phenomena.

Special attention was given to the detection and adjustment of temperature which shall be comprised between 230-:-240° C. and also to the methanol discharge system from the reactor, and to handling.

Table 1 further shows the most important data of the methanol production with different membrane reactors.

TABLE 1

Number and type of membrane reactors required to transform all the $CO_2$ contained in the flue gas of a 1320 MW coal dust thermo-electrical plant into methanol.

| Membrane reactor Num. membr. Ø20 mm | Inlet of $CO_2$ Kg/h | Inlet of $H_2$ Kg/h | Catalyst. Kg/react. | Num. reactors for producing 685,286 Kg/h Methanol | Methanol kg/h |
|---|---|---|---|---|---|
| 82 | 1,158 | 3,500 | 107 | 556 | 1,230 |
| 1,500 | 19,700 | 59,500 | 1,820 | 33 | 20,910 |
| 2,500 | 32,500 | 98,200 | 3,000 | 20 | 34,500 |

The calculations are precautionary considering a conversion lower than 25% per passage.

Since the range of temperatures that concerns the methanol synthesis varies in the range 200-:-400° C., high pressure equipment and all the parts that contact the synthesis mixture must be made of special materials. The patent literature relative to the results of corrosion tests and of the reactions that may take care in the synthesis of methanol is very rich; the heat and energy indexes are shown for each of them up to the temperature of 350° C. (which can be regarded as the operating temperature of the syntheses currently realised at industrial level). The main variables that affect the process, favouring the formation of one or the other indicated products, besides the type of internal equipment, are the nature and the activity of the catalyst, composition, temperature and pressure of the gas entering the reactor and the spatial speed of the gas in the catalytic mass.

The patent literature relative to catalysts for the synthesis of methanol is very rich; a quite detailed description of the various types of catalysts proposed was made by Dolgov. On one point the various experimenters agree and namely on the absolute exclusion of the elements of the iron group, which catalyze the reaction of formation of the methane.

In practice, however, we can distinguish two groups of usable catalysts: those based on copper oxide and those based on zinc oxide.

The copper oxide catalysts, which had been a little difficult to use, were considerably improved by Synetix, which developed a new process at low pressure which operates at 35-55 bar and 200-300° C., becoming the most widely used one. The catalysts used for the synthesis of methanol are based on copper. Many techniques have been developed to stabilize the catalysts. Highly active and selective catalysts suitable for large production of methanol today are those incorporating $Cu/ZnO/Al_2O_3$. These catalysts are already active at 200° C. and selective for the formation of $H_2$ and $CO_2$.

From a theoretical point of view, the conversion of the methanol, in relation to a traditional reactor, can be increased by following two different paths:

Recycle the non reacted part of gas following separation of water and methanol. This method is the one currently followed, however it does not provide any benefit to the dimension of the reaction and the quantity of catalyst.

Remove the reaction products during the chemical reaction.

This can be done by utilizing the membrane reactors (MRs) which combine the characteristics of the reaction with those of the separators.

The, use of membrane reactors can increase both the yield in methanol and a savings of the excess reagent (hydrogen).

A membrane reactor can be used for the synthesis of methanol in different ways. The first method is that of utilizing dense membranes of palladium to feed, the hydrogen in a controlled manner into the reaction environment and avoid its subsequent separation.

Instead, in the second one, the membrane reactor has the purpose of continuously removing from the reaction environment one or more products to improve the conversions for passage and extract the pure product or products. In literature there are works that describe the use of MRs for the production of methanol.

Table 2 gives the best results obtained from various authors with the MRs compared to the traditional ones.

TABLE 2

Improvements obtained by using MRs in the production of methanol.

| Membranes | Results compared to TR | References |
|---|---|---|
| Lithiated Nafion | 40% improvement in the yield in Methanol | [1] |
| Pd—Ag | 9% improvement in the conversion at balance | [2] |
| Lithiated Nafion | 40% improvement in the yield in Methanol | [3] |
| Silicone rubber/ceramic | 22% improvement in the conversion | [4] |
| Zeolite MOR/ZSM-5/chabazite | 60% improvement in the conversion | [5] |
| Zeolite A - type | 132% improvement in the conversion | [6] |

At ITM-CNR various works have been carried out on this reaction conducted in membrane reactors. In particular, as reported by Gallucci et al. [6], the use of zeolitic membranes registered an increase in the conversion of 132% compared to the traditional reactor operating at the same conditions of temperature and pressure. These results were obtained at temperatures below 240° C. A temperature regulator will be provided to maintaining it in the reactor within 230-:-240° C. In fact, at these temperatures the methanol and the water condense in the pores of the zeolite and are separated selectively from the environment of reaction. We must remember that also in the case of membrane reactors, the non converted reagents can be recycled to arrive at a complete conversion.

The zeolites, crystalline aluminosilicates with high chemical, thermal and mechanical stability, have pores with molecular dimensions. Moreover, by increasing the molar ratio Si/Al, during the synthesis phase, it becomes possible to change their nature from hydrophilic to hydrophobic. Consequently, these materials, as membranes, provide the possibility of separating continuously mixtures of liquid and gaseous substances based on the differences in form and dimension (as for example isomers [7], azeotropic mixtures and compounds having the same molecular weight but different form [8]). Recently, for example, in Japan an industrial plant was realized for the dehydration of alcohols through pervaporation with hydrophilic tubular membranes of zeolite (A) [9]. Moreover, the zeolitic membranes because of their chemical and thermal stability are also studied for their possible use in membrane reactors.

The self-supported zeolitic membranes are extremely fragile. In consideration of this, it is necessary to use supports (alumina, stainless steel) on which zeolitic layers are grown to obtain the desired mechanical resistance. However, their use at the industrial level is highly limited by problems of reproducibility in the preparation stage [8] and presence of intracrystalline defects in the zeolitic layer [10].

With reference to operating temperatures of 230° C. and pressure of 50 bars, calculations have been performed by considering both the traditional reactor and the membrane reactor in which the catalyst is placed outside the membranes. In the following table are given the number of reactors necessary to convert the entire quantity of carbon dioxide (600,000 $Nm^3/h$) produced by the Serbia plant.

TABLE 3

| Reactor Type | Internal diameter of reactor mm | Internal diameter of membrane mm | kg · Cat per reactor | Number of reactors | kg/h Methanol |
|---|---|---|---|---|---|
| Traditional | 260 | — | 57 | 2670 | 642455 |
| Traditional | 400 | — | 143 | 1044 | 642455 |
| Membrane | 250 | 6.7 | 49 | 1215 | 685286 |
| Membrane | 400 | 20 | 107 | 556 | 685286 |

In the case of traditional reactors, water and methanol must be condensed downstream of the reactor and before the recirculation. For the membrane reactor this operation is not necessary.

Moreover, it must be emphasized that, in the case of the membrane reactors, the calculation was done cautiously by considering a conversion below 25%. Obviously, if we manage to increase the conversion, the number of membrane reactors will diminish.

The ratio of $H_2/CO_2$ supply for the reaction is 3/1 in molar (and volumetric) terms. So that the requirement of $H_2$ is 1,800,000 $Nm^3/h$ equal to 161 ton/h of hydrogen.

FIG. 18. Plan view 18.1 and perspective view 18.2 of the AST-CNR/ITM plant for a coal dust thermo-electrical plant of 300-:-350 MWel. The module is made up of 12 reaction towers connected by the flue gas distribution system 181 which, captured by the duct of flue gases of the plant is distributed for processing to the towers through motorized gates commanded by the general control of the plant.

The layout typically has dimensions of 24.00×14.00 meters and has available 9 storeys for a total of 3,024 $m^2$ of useful surface, where the complementary installations are allocated for the processing and collection of polluting material, and a dead freight volume of 110,000 $m^3$. The plant, made up of twelve reaction towers, is capable of processing between 1,100,000 and 1,300,000 $m^3/h$ of dry flue gases (scfm-dry) corresponding to the emissions of a supercritical coal dust thermo-electrical plant with power of 300-:-350 MWel that are the average sizes of the unit modules for thermo-electrical plants in Europe and the USA respectively.

FIG. 19. Plan view (FIG. 19.1), front view (FIG. 19.2) and perspective view (FIG. 19.3) of the. AST-CNR/ITM plant for a coal dust thermo-electrical plant of 1320 MWel made up of 60 reaction towers designed for the supercritical coal dust thermo-electrical plant of AST SERBIA. The plan has dimensions of 120.00×14.00 meters for a building volume of 62,000 $m^3$, arranged on 9 storeys for a total of 9,500 $m^2$ where the complementary plants are allocated for the processing and collection of the polluting materials. The plant, made up of sixty reaction towers, is capable of processing 4,800,000 $m^3/h$ of dry flue gas (scfm-dry) corresponding to the emissions of a supercritical coal dust thermo-electrical plant with power of 1,320 MWel.

Description of a Preferred Embodiment

The modular plant for removing the pollutants from flue gases produced by industrial processes according to this invention, which makes up the so-called "AST-CNR/ITM system" at zero emission for the treatment of flue gases is composed of prefabricated modular elements, with programmed and automatic operation, which form the different sections of the reactions towers. The membrane reactors for the production of methanol of AST-CNR/ITM design also form part of the plant as will be explained hereinafter also with the use of the attached figures.

The towers are also prefabricated and modular with automatic operation, and are used for the removal of pollutants (such as NOx, SOx, submicron particulates, heavy metals, in particular mercury) and for the capture of $CO_2$ from the flue gases which form during combustion of fossil fuels in the plants that in their processes use these types of fuels, such as:

THERMO-ELECTRIC POWER PLANT of carbon, oil, gas,
COGENERATION PLANTS for the production of electric energy and superheated steam,
REFINERIES,
CEMENT WORKS,
IRONWORKS,
STEELWORKS,
CHEMICAL PLANTS,
INCINERATION PLANTS FOR SOLID URBAN WASTE, The plant according to the invention includes electrolysers of per se known type, such as for example those marketed by the SIEMENS and GENERAL ELECTRIC companies, necessary for the production of hydrogen and oxygen.

The block diagram of FIGS. 1 and 1A shows the processes of the "ZERO EMISSION AST-CNR/ITM SYSTEM".

The "AST-CNR/ITM" process overall includes four types of integrated treatments, the first one relative to flue gas treatment, the second to the separation of the $CO_2$ from the flue gas, the third to the production of hydrogen and oxygen by electrolysis at high temperature and thermo-chemical water splitting, the fourth to the production of methanol starting from the $CO_2$.

The flue gas treatment is based on processes of chemical conversion, absorption (chemical-physical process consisting in the adhesion and concentration of the substances dissolved or dispersed into the atmosphere on the surface of a body), oxidation of the combustion gas components, and corresponding combinations. All these processes occur in the left columns of the block diagram of FIG. 1A, where each of the boxes represents a section of the reaction tower, illustrated also in FIGS. 18 and 19. These treatments are conducted on the flue gas withdrawn from the ducts that carry said flue gas, treated in advance in the electrostatic precipitator of the plant, to other plants or to the chimney.

The base module AST-CNR/ITM is made up of a reaction tower A constituted by four sections (FIG. 6.1) formed by cylinders preferably having a diameter of 2.40-:-2.50 m and a height of about 8.50 m. The sections are arranged vertically one on top of the other and inside they have a principal central duct inside which the flue gas passes and in which the pollutants are removed or captured, with dry or damp procedures and the use of appropriate catalysts.

The sections are the following:

First section—Treatment of the fine particulates, fine dust with a diameter of between 100 μm and 0.01 μm, since the larger sized dust has already been removed by the electrostatic precipitators and by the bag filters previously placed at the entrance of the flue gas in each tower;

Second section—Treatment of the pollutants containing sulphur oxides and optionally aromatic hydrocarbons;

Third section—Treatment of the pollutants containing nitrogen oxides and optionally aromatic hydrocarbons;

Fourth section—Capture of carbon dioxide.

Each tower A can typically have the following dimensions: diameter 2.40 m and height 34.00 m, can treat 70,000 $m^3$/h of dry flue gas (scfm-dry) or 125,000 $m^3$/h of wet flue gas (acfm-wet).

Each tower and each section are connected to the next ones through pipes that typically can have a diameter of around 0.75 m, provided with shut-off valves and/or fans per se known.

The reaction towers A can be set up differently depending on the requirements of the plants that must be treated and for each of which will studied the most appropriate measures. Advantageously, thanks to the modularity of the towers and their simplicity of set-up, it is possible to test the flue gas to be treated directly in pilot plants, constituted by a single tower of real dimensions.

FIG. 6 illustrates some example of the types of assembly of the towers as a function of the nature of the flue gas, whose treatment depends:

on the type of industry to be reclaimed,
on the treatment plants already installed in them and that must be integrated,
on the current environmental regulations,
on the financial plans available to the industries for the regulatory adjustment,
on the fact that the plants are of new construction.

The disposal plants according to the invention have been designed in order to be built, assembled and tested in the respective construction factories to then be dismantled and shipped on roads and railways, thanks for their dimensions, kept within the limits of the shapes permitted.

This permits a simple, fast, safe, versatile and economical assembly on site and also allows the already existing disposal plants to be updated in the thermo-electrical plants, in the refineries, in the incinerators by integrating them with the prefabricated AST-CNR/ITM elements of the invention.

The reaction towers A can operate with pressures up to 5 bar and this allows great savings in the construction phase because the base element will be able to treat quantities of flue gas more than double compared to the 70,000 $Nm^3$/h provided for in the base element operating up to 2 bar. If the towers operate at pressures of 5 bar they can treat in the base element more than 150,000 $Nm^3$/h and therefore the plants will be reduced since only half of the reaction towers will be needed to treat equal quantities of flue gas and moreover its maintenance will be simpler and less expensive.

The towers are connected among them at inlet down low and on outlet up high through pipes that carry the flue gas to be treated and distributes them to the individual towers and collects them top-edge, once treated, to convey them to the outlet of the plant. Moreover, each section is provided with inlet pipes/ducts (not shown) for the reagents and outlet pipes/ducts (not shown) for the removal and/or recirculation of eventual final products.

Load Bearing Structure

The bearing structure of the reaction towers A, represented in FIGS. 8.2, 8.3 and 8.4, is made with erected frames, calculated to support, in addition to the permanent loads of the structure itself and the technical equipment, also the loads from the accumulation of reagents and materials resulting from the process, and the loads transmitted by the people who work in the plant. The sizing is within the capacity of the man skilled in the art.

Frames 820 are made with beams and pillars created with broad flanged beams of commercial steel, assembled in the workshop in sections with shapes in sizes that can be transported normally, in order to reduce to a minimum the building operations.

Furthermore, the structure has the peculiarity of allowing the replacement of a section of the reaction tower A, whatever its position in tower A, without having to dismantle the entire reaction tower. In other words, the set up allows the removal of a single section, for repairing, and its substitution with another section ready and available in house, without the operation requiring the elimination of the flue gas from the circuit, of an entire module of the plant. It is therefore possible to exclude a single tower from the operation of the plant without stopping it. Furthermore, the section removed can be substituted with another similar section, that will be available at the plant, sending the removed one to the construction factory for its overhaul. This possibility makes the plant much more reliable and less expensive since it can guarantee the operation of the plant for all the 8,760 hours available per year, and can program a maintenance which excludes in turn one or two reaction towers from the process.

Module Assembly

The assembling of the reaction towers takes place according to conditions per se known, by setting up the foundations of the structure and the connections with the duct of the gas flue, with the networks of the utilities and controls. Then the assembling of the bearing structure described above is done, which arrives at the building site already assembled in sections normally transportable, treated for protection against corrosion with special galvanizing and paints. The assembling is done with welded flanges. Then the prefabricated floors are assembled, the sections of the tower are put in place, the complementary equipment and accessory machinery are mounted and finally the wiring for the connection of the controls of the individual sections of each tower is done, and that of the different towers with the general control of the plant according to a hierarchical system.

Control System

The data control and acquisition system of the sections of the reaction towers permits the automatic performance of the zero calibration measurements and the safety procedures. The status of the system and the individual devices is displayed on a panel, on the displays in the control room and can be checked in real time from any position through the network.

The processing system and the presentation of the data can be easily configured and managed by the operator. The acquisition of the data from the field, its validation, the processing and presentation of the hourly, daily, weekly and monthly averages are done in accordance with current regulations.

The system gives in real time the capacity flow of the flue gas, their temperature and the contents in CO, $CO_2$, $O_2$, SOx, NOx, particulates and metals.

Based on the values of the capacity flow, the program of management takes care of putting into operation the number of reaction towers capable of handling the total cleaning of the flue gas.

Usually the number of towers put into operation is not all of those available, which intervene simultaneously only during peak production.

This solution allows considerable savings in the operation of the plant both in terms of consumption of reagents and catalysts, and in the consumption of energy necessary to operate the towers.

The program of management of the plant also takes care of managing and organizing a turnover of work for the reaction towers, in order to organize an equal management of work for all the towers and therefore create a system of equal wear on the towers.

This is a peculiarity of the AST-CNR/ITM plants which makes them unique among those utilized in plants built today and which permits realizing considerable savings both in management and, more importantly, in the life of the plants themselves.

Analysis for the Process Control with FT-IR Dual Cell Technology

The FT-IR dual cell process control (known per se) is characterized in that the output signal from the interferometer is split in two optic paths and sent to two different cells.

The sample of gas taken respectively upstream and downstream the removal system is then sent to them.

A detector is assigned to each cell, the analysis is done automatically and simultaneously by the two withdrawal points.

Furthermore, from a different optic path, different measurements are also allowed, so the dual cell permits the evaluation of the efficiency of the system being measured and thus allows the correct regulation of the process and a considerable saving in reagents.

Alternately, it is possible to utilize the instrument to monitor two gas streams belonging to two different lines, achieving considerable economic savings.

First Section of the Reaction Tower

The first section of the AST-CNR/ITM reaction towers is equipped for the elimination of mercury and other metals, after removal of the fine particulates.

The solids are captured with an electrostatic precipitator, also called ESP, of the wet type (indicated as WESP-Wet ElectroStatic Precipitator) together with the oxides of heavy metals, fluorides and chlorides. These, together with the washing water, go to a dispenser, outside the tower, loaded with limestone, in which the polluting substances are calcined. The remaining water is treated in an ion exchanger with caustic soda to eliminate the chlorides and is recycled again inside the water treatment system using membrane plants.

The operation of the WESP is influenced by the temperature of the flue gas which determines the electric characteristics that the electrodes must have for the corona effect to start and the pollutants to precipitate. For a given applied voltage, the dispersion current increases with the rise in temperature. The temperature of the flue gas which enters the WESP is controlled and is generally quite constant. The temperature of the flue gas is controlled by the temperature of the water of the plant which can be modified to improve the performance of WESP. The composition of the flue gas determines furthermore the electric characteristics of the WESP.

It is therefore important to know exactly the impurities contained in the flue gas both to be able to exactly plan the WESP and to size the plants for the removal of the impurities from the wastewater of the plant. Some impurities are removed easily while other will be more difficult. For this reason, it is important to know the type and the concentration of all the pollutants contained in the flue gas (the expert of the branch knows what to do).

Furthermore, if the composition of the flue gas varies during the use of the WESP, it is instantly evaluated by the control system so that the electric characteristics of the WESP are also modified instantly to guarantee its perfect operation.

Generally, the pollutants are present in the following forms:

| Impurities | Form of impurity | Chemical formula |
|---|---|---|
| Fluoride | Powder | HF |
| Chloride | Powder | HCl |
| Arsenic | Oxide, element | $As_2O_3$, As |
| Selenium | Oxide, element | SeO, Se |
| Mercury | Element | Hg |
| Zinc | Sulphate | $ZnSO_4$ |
| Lead | Sulphate, element | $PbSO_4$, Pb |
| Copper | Sulphate | $CuSO_4$ |

Acid fog, copper, nickel and iron and the acids are generally considered easy to collect. The more difficult impurities include zinc, lead, arsenic and antimony. The flue gases, in other words the combustion gases, which enter the first section of the reaction tower at a temperature of approximately 170° C., are saturated and cooled through a heat recovery system and with the injection of the process water.

Because of the excess oxygen and the high combustion temperatures of the plant for removal of the coarse particulates, a part of the sulphurous anhydride is dissolved as sulphate and removed from the reaction tower together with the treatment water, the solids captured with the electrostatic precipitator, the oxides of the heavy metals, the fluorides and the chlorides. It goes to a dispenser loaded with limestone in which the polluting substances are calcined. The remaining water is treated in an ion exchanger with caustic soda to eliminate the chlorides and is recycled again inside the water treatment system.

FIG. 9.2 is a transparent axonometry of the first section, with particular reference to the West-ESP (wet). The flue gases entering from the bottom pass through a heat exchanger, in fact, to avoid their having a high degree of humidity, they undergo cooling through a heat exchanger, coil-type for example, which lowers the temperature from 190-:-170° C. to 50-:-40 ° C. The flue gases are then taken by pipes 931 and 932 where they are subjected to an electric field.

The AST-CNR/ITM electrostatic precipitators have a high efficiency in blocking the submicron particles and use electrostatic forces to remove the particles suspended in the flow of the flue gas.

The operation of the AST-CNR/ITM precipitators includes the following stages:
- electrically charge the submicron particles through the corona effect determined by a difference in voltage (around 50-:-65 kvolts) between a copper electrode, with anchorages insulated electrically and placed high and low, in the centre of the pipes that make up the honeycomb tube bundle, the walls of which, electrically charged with negative polarity, opposite of that of the electrodes, form the collection area of the particulate matter (FIG. 9.3). The particles, once charged electrically, are attracted towards zones with opposite charge (walls of the pipes) and collect thereon;
- remove the particles that have been accumulated on the walls of the piping.

The speed of the flue gas inside the ESP is measured in such a way as to reduce the risk of dragging solid particles which have accumulated on the collection plates, constituted by the walls of the tube bundle. Compared to other systems for removal of particulate matter, the ESP AST-CNR/ITM are characterized by the low amounts of load losses due to the particular processing of the electrodes which facilitate the onset of the corona effect at lower kV which vary in general between 20 and 100 Pa.

The electrodes and the piping are washed periodically by a programmed system that blocks the supply of electricity in the electrodes and at the same time opens the supply circuit of the sprinklers which spray water for the washing of the electrodes and the piping, thus removing the accumulated particles.

The ESPs AST-CRN/ITM is used for the removal of the free flow particles (that is, the particles contained in the flue gases before the first washing in the first section of the reaction tower) and is taken in the first section to the wet ESP. It is made up of a washing plant to block the VOCs. The liquid is the one coming from the washing of the WESP specified above, usually made up of water and detergents, and continuously removes the particles. The wet ESPs is always in operation. It is widely used for applications where the gas to be treated is hot, has a high humidity content and contains sticky or submicron particles that cannot be treated with other methods.

The WET-ESP section of AST-CNR/ITM, illustrated in FIG. 9.2 in transparent axonometry, includes significant improvements in technology for the efficiency of operation when in the pollutants to be removed from the flue gases mercury and its compounds are present.

The honeycomb configuration of the electrostatic precipitator (FIGS. 9.2 and 9.3) is advantageously formed by a circular configuration so that the piping in this case is made up of side by side pipes. The arrangement of the electrodes remains basically the "multipoint" one of FIG. 10.1 and no interruption of operation that is not programmed is required for cleaning.

Removal of Mercury

Often coal contains traces of mercury as contaminant. When coal is burnt, mercury volatilizes as mercury vapour and mixes with the flue gases. When the coal also contains selenium it is released, during combustion, together with the mercury forming HgSe and both can be easily removed from the flue gases in the wet-ESP, to then be sent to the other sections for removal of other pollutants.

In the wet electrostatic precipitation phase, mercury reacts with the sulphurous anhydride and the oxygen present in the flue gases, thus forming mercury sulphate according to the reaction:

$$Hg(g)+SO_2(g)+O_2(g) \Longrightarrow HgSO_4$$

The mercury sulphate will also be easily removed from the flue gases in the wet-ESP before the electrostatic precipitation phase.

The mercury that remains free goes on along the reaction tower as mercury vapour.

If not treated further, mercury enters in the section of the reaction tower where the removal of SOx occurs, thus contaminating the sulphur and the calcium sulphate (chalk) which are obtained as products of the removal of the SOx.

The sulphur contaminated with mercury cannot be used in industries whose products enter the feed cycle: consequently, it is preferable to remove the mercury from the sulphur to obtain a product better marketable and this must always be performed in the first section of the reaction tower.

Removal of Mercury—Outokumpu Method

Mercury can be treated while it is in the flue gas with the method of removal in gaseous phase (known as Outokumpu process). It is advantageous to remove mercury in the first section of the reaction tower in that it highly reduces the probability of polluting the other products obtained in the subsequent treatments performer in the reaction tower (sulphur, chalk, etc.), which can be profitably reused as secondary raw materials.

The Outokumpu process converts the elementary mercury contained in the flue gas according to the reaction:

$$Hg+H_2SO_4 \rightarrow \tfrac{1}{2}O_2+HgSO_4+H_2O$$

The mercury gas and the other metals are captured with $H_2SO_4$ in the amount of 80-90% at a temperature of 150-180° C. The acid is recycled until the solution is not saturated with $HgSO_4$ and precipitation starts.

The $HgSO_4$ crystals are then separated in a thickener (not shown). In the washing plant (not shown) other polluting agents besides mercury are removed from the flue gas.

The solids collected in the thickener, furthermore, can contain iron, zinc, copper, selenium, etc. Mercury can be recovered by mixing first the solids precipitated with calcium oxide and then by heating the mixture to distill and separate the mercury. The selenium remains in the mixture in form of calcium selenite (these phases occur in complementary plants).

By using this method it is not possible to recover the heat from the flue gases before they are put into the first section of the reaction tower, but heat can be recovered in the piping by providing it with a skirt or cavity in which a fluid is present, usually water, for the thermal recovery.

Removal of Mercury—BOLIDEN Process

The Boliden process is particularly suited to low concentrations of mercury and consists in passing the flue gas through selenium filters made with inert porous material soaked in selenious acid. The flow of the flue gas that passes through it, dries the filter so that the red amorphous selenium precipitates according to the reaction:

$$SeO_2+H_2O=H_2SeO_3$$

The selenium oxide in water gives selenious acid.

The selenious acid is produced with this reaction also during washing with water of the flue gases of selenium dioxide which evolved during the treatment of the anode sludge of electrolysis of the copper.

This is a weak acid ($K_1^{(25.\ C)}=3\mu\ 10^{-3}$), solid at room temperature, very soluble in water (~63% at 25° C.), which is oxidized by strong oxidants of selenic acid, and reduced by strong selenium reducers. The sulphur in its tetravalent form, such as sulphur dioxide, can in certain conditions reduce the selenium from its tetravalent form to its elementary form.

$$H_2SeO_3+2SO_2+H_2O=Se+2H_2SO_4$$

During precipitation of the metallic selenium from selenious acid through sulphur dioxide, the temperature of the solution must be maintained at 25-:-30° C. so that the selenium deposits as sludge in a form that can be easily discharged from the precipitators. Beyond this range of temperature, the mud becomes plastic and is difficult to remove. The mud produced is then boiled to coagulate the amorphous red selenium and to convert to crystalline form. The solutions of selenious acid contain tellurium. In the presence of sulphuric acid, the precipitation of selenium is selective. Instead in the presence of hydrochloric acid the tellurium also precipitates and, at high concentrations, of hydrochloric acid, both the metals dissolve forming chlorides. The salts deriving from it are the selenites.

The red amorphous selenium reacts with the mercury of the flue gas forming HgSe, mercury selenide. The contact time in the filter is approximately 1-2 seconds. The filter continues to be effective until the level of mercury in the filter reaches 10-15%. The filter then is treated to recovery the mercury and to regenerate the selenium. The filter will remove approximately 90% of the mercury received. Like the filter with selenious acid, this process of removal depends on the presence of elementary amorphous selenium to react with the elementary mercury in the gas. The concentration of the selenious acid is between 20 and 40%. The lower concentrations of selenium will create. highly soluble residues of the selenium and the sulphur which make them inefficient in the reaction with the mercury in the gas.

At the higher acid concentrations, the supply of oxidation of the acid will cause the dioxide or the selenite of the selenium which has formed. If the flue gas that is treated contains sufficient selenium, it is not a requirement to add the selenium to the solution of the washing plant. The washing plant of the selenium is suited to removing the large relative quantities of mercury in the flue gas and has an efficiency of about 90%.

For the Boliden process, the honeycomb tubing is used as described in the beginning and illustrated in FIG. 11.

Removal of the Mercury—BOLIDEN/Norzink Process

This process is based on the oxidation of the mercury vapour contained in the flue gases with mercury chloride to create mercurous chloride according to the reaction:

$$HgCl_2+Hg \rightarrow Hg_2Cl_2$$

A solution of mercuric chloride containing sufficient quantity of $HgCl_2$ is circulated in a tower of various porous ceramic rings soaked in mercuric chloride. The process flue gases which contain the mercury pass through the ceramic tower where the mercury reacts with the mercuric chloride to create mercurous chloride.

The mercurous chloride is insoluble and precipitates in the solution. From the main circulating flow of the ceramic tower a lateral flow is separated (not shown) aimed towards the primary decanter (not shown) where the mercurous chloride is deposited in the lower part of a tank (not shown).

The clarified solution spills over again to the tank and is pumped to the reagent tower. The solids collected from the bottom of the primary decanter flow to the secondary decanter (not shown) where the concentration of mercurous chloride is lower. In the secondary decanter, zinc powder can be added to promote precipitation of the mercury from the solution. The solids of the secondary decanter are discharged in deposits (not shown) from which they are sent either for sale or to other manufacturing.

The washing process removes the mercurous chloride from the solution. If the concentration of mercurous chloride is not kept within the parameters calculated it will become inefficient as reagent solution. To regenerate it, a part of the mercurous chloride collected will serve for the purpose.

FIG. 11 shows in detail the reactor for the mercury of FIG. 9.2.

Second Section of the Reaction Tower—Removal of the SOx

The flue gases in output from the collection plant of the particulate matter and before entering into the second section are washed in advance with a watery acid solution to eliminate HCl, HF and residual particulate matter without absorbing the $SO_2$ contained in the flue gas. The processes of desulphurization can be classified in processes with or without recovery.

The products recovered are, depending on the cases, $SO_2$, $H_2SO_4$, $(NH_4)_2SO_4$, $NH_3$, $CaSO_4$, $H_2$.

The processes without recovery are those that, by achieving the removal of the $SO_2$ through a reagent whose regeneration is not economically convenient, cause a consumption of reagent proportional to the quantity of $SO_2$ removed from the current of flue gas. These processes, generally less expensive in the plant phase, present however the problem of disposal of considerable quantities of products resulting from the treatment, basically composed by a mixture of sulphites and sulphates in the form of mud or highly pollutant solid products.

The processes with recovery are those that allow both the chemical or thermal regeneration of the absorbent for its reuse and the recovery of the $SO_2$ to obtain a marketable product such as liquid $SO_2$, sulphur or $H_2SO_4$.

Despite the potential advantage resulting from the sale of the products, from the recovery of the reagent and from the absence of by-products to be disposed of, these processes have not been widely distributed up to now because, due to the consumption of energy connected with the regeneration of the reagent and of the actual consumption of reagent due to the formation of compounds which cannot be regenerated, the cost of the desulphurization is generally higher than that of processes without recovery.

In the sphere of the classification between processes with and without recovery, another breakdown can be made based on the chemical-physical conditions in which the treatment of the gaseous current of the flue gas to be purified occurs.

The wet processes are based on the absorption of the $SO_2$ with a watery solution/suspension. These processes, characterized by a multiplicity of engineering choices inherent to the operating conditions, to the flow charts, to the type and concentration of the absorbent solution, are those that have had greater proliferation.

Generally we use absorption towers with light packing are used where the following balances come into play:

$$SO_2(g) + H_2O(l) \leftrightarrows SO_2.H_2O \; (aq) \quad (1.1)$$

$$SO_2.H_2O(aq) \leftrightarrows HSO_3^-(aq) + H^+ \quad (1.2)$$

$$HSO_3^-(aq) \leftrightarrows SO_3^{-2}(aq) + H^+ \quad (1.3)$$

The AST-CNR/ITM technology for the removal of the SOx is a Flue Gas Desulphurization (FGD). This method was selected to achieve a "system of zero emission" and is based on the utilization of what is contained in the flue gas for obtain a production of hydrogen necessary for the AST process.

Relative to the actual limits of emission; the FGD systems represent an essential component of the thermo-electrical carbon plants, especially is of medium/high level of sulphur.

In fact, the concentration of $SO_2$ (under normal conditions and with oxygen at 6%) in the flue gas produced by a steam generator supplied with a carbon having 3% of sulphur is equal to approximately 6000 mg/Nm³ which, in order to fall within the regulatory limits valid for large plants (>200 mg/Nm³) requires an efficiency of desulphurization of almost 97%.

Obviously, the efficiency of desulphurization required of the FGD system increases with the level of sulphur in the carbon, thereby equaling over 98% for a carbon with 6-:-7% of sulphur, such as the carbon made up from peat and oil coke.

Of all the FGD processes proposed and developed over the last decades, those that up to now have experienced an effective circulation on an industrial scale are basically the wet processes (wet scrubbers), the semi-dry processes (spray-dry scrubbers), the dry process (dry scrubbers) and some regenerating with the combined removal of SOx and NOx processes.

The wet, semi-wet and dry processes remove the $SO_2$ present in the gases burned through injection of a basic absorbent, in most cases based on calcium, and often simply represented by calcium carbonate.

These processes produce solid residues that, in relation to the type of FGD system, can be more properly by-products with a commercial value, such as chalk from the wet FGD systems, and the sale of which provides a profit, or hazardous waste containing high percentages of sulphates and sulphites mixes with loose ashes, in the case of the semi-dry and dry FGD systems, whose disposal is discharge instead causes a burden.

This aspect appears extremely important in case one considers that the FGD systems produce approximately 3-:-4 tons of solid residues for each ton of $SO_2$ removed from the flue gas, so that a power plant of 500-:-600 MW supplied by a carbon with high sulphur content can produce annually approximately 500-:-600 thousand tons of solid residues, by consuming 250-:-300 thousand tons of limestone.

In regenerating processes, on the contrary, during the initial absorption phase of the $SO_2$ by an absorbent there follows a phase of regeneration, with release of liquid $SO_2$, or sulphuric acid ($H_2SO_4$) or finally pure sulphur.

The most interesting combined processes for the removal of the SOx and the NOx operate according to catalytic processes and do not require absorbents and do not produce solid residues, but marketable by-products such as sulphuric acid.

Against the greater initial costs and, in general, the higher operating costs, the regenerating and combined processes present the not negligible advantage of high efficiency in the removal of the SOx together with no consumption of limestone and the no production of solid residues.

The world market of FGD systems is dominated by the wet process technology, with approximately 87% of the overall installed capacity, following which are the semi-dry systems (8%), the dry systems (2%) and the regenerating processes, combined or of other type (the remaining 3%).

In the second section of the AST-CNR/ITM reaction tower (FIG. 12), the sulphurous anhydride is eliminated by using an amine, typically ipropylamine (DPA), as additive through catalyzing washing trays 1222, 1224 and 1226 and with the extraction of the process water. In practice the trays contain solid supports (packs of ceramic elements) which are drizzled with water containing dipropylamine.

The water is then removed and divided in a stripping column and in a cooling device of the gas, outside the reaction tower.

The remaining gases are passed to the next section of the reaction tower, the third section.

Third Section of the Reaction Towers for the Removal of the NOx

With the term "nitrogen oxides" we generally mean all the nitrogen oxide and dioxide, even though in reality they constitute a more complex mixture as summarized in Table 4.

TABLE 4

Components of the nitrogen oxides

| Compound | Formula |
|---|---|
| Nitrogen dioxide | $N_2O$ |
| Nitrogen oxide | NO |
| Nitrogen dioxide (Nitrous anhydride) | $N_2O_3$ |
| Nitrogen dioxide | $NO_2$ |
| Nitrogen tetroxide | $N_2O_4$ |
| Nitrogen pentoxide (Nitric anhydride) | $N_2O_5$ |

The small residual part of the sulphurous anhydride coming from the second section is converted in the third section (FIG. 13) of the reaction tower through catalyzing trays in them and by contact with the ammonia solution. The sulphate resulting from the contact of the ammonia with the flue gas is processed in the electrolysis.

When sulphuric acid is added to the ammonium nitrate, nitrogen dioxide and ammonium sulphate is obtained.

In the dry phase, in the first part of the reaction tower, $NO_2$ is added in stoichiometric quantity to the gas mixture of NOx and is completely mixed by the circulation trays.

During the following wet phase, in the second part of the third section, the mixture of the NOx gas passes along a certain number of contact trays together with ammonia and is converted into ammonia nitrate.

The nitrogen dioxide surplus can be converted with water into nitric acid in a stripping and reduced to nitrogen in a small adsorbent catalyst by using ammonia in the complementary plants.

The ammonia sulphate is the by-product of the electrolysis and is done in complementary plants in ammonia and sulphuric acid.

The ammonia is the reactive in the third section of the tower. The sulphuric acid is used for the separation of the nitrate. When sulphuric acid is added to the ammonia nitrate, one gets nitrogen dioxide and ammonium sulphate.

Fourth Section of the Reaction Towers—Capture of the $CO_2$

In the fourth section of the reaction tower (FIG. 14) the flue gas arrives after having been treated in the third section.

They are basically made up of nitrogen, steam and carbon dioxide since in the previous treatments the pollutants are eliminated.

The concentration of the $CO_2$ depends on the type of fuel which generated the flue gas emitted and that, in percentage on the volume of the flue gas, varies from 14% for coal power plants, to 8% for natural gas power plants, to 4% for natural gas power plants with combined cycle and in other ratios for the other production plants.

By quantifying these percentages, a coal-dust thermo-electrical plant of 1320 MW of power emits in one year about 8 million tons of $CO_2$ Traditionally the $CO_2$ so captured is subsequently subjected to different processes according to the selected confinement or utilization type; however its shipment to a place other than where it was captured is provided, it is subjected to a pressurization process in order to pass from the gaseous state to the liquid state with consequent reduction of volumes.

For the capture of $CO_2$, the fourth section is made up of an adsorption tower (MEA amine) in which the $CO_2$ is captured by aminic substances (MEA) which subsequently are put into a stripping tower where the heated aminic liquid releases the concentrated $CO_2$ regenerating the adsorption compound.

The $CO_2$ so captured can be subsequently subjected to various processes depending on the type of preselected confinement or utilization. For example, pressurization, or can be transformed in methanol as hereinafter described.

The $CO_2$ is confined in repositories already exploited and exhausted of gas, oil or in marine depths.

AST-CNR/ITM System of Separation of the $CO_2$ by a Gaseous Current Consisting of $N_2$ and $CO_2$ Through Membranes.

The following description and the calculations refer to the separation of the $CO_2$ from a gaseous current consisting of $N_2$ and $CO_2$ (Flue gas released by the third section of the AST-CNR/ITM reaction towers after the removal of the pollutants: particulate matters, metals, SOx and NOx which occurred in the first three AST sections).

This membrane solution is an alternative to the previously described amines separation in the fourth section of the AST-CNR/ITM reaction towers and illustrated in FIG. 15.

A gaseous current (flue gas) is taken into consideration with a flow rate of 4600000 $Nm^3/h$, and is basically made up of nitrogen, watery vapour and carbon dioxide since in the treatments previously described the pollutants were removed in the following concentrations: $CO_2$: 14%, $N_2$: 86%

Starting from the above gaseous rate, by the use of membranes it is possible to obtain a gaseous current rich in $CO_2$. [R. W. Baker, *Membrane technology and applications*, J. Wiley & Sons, (2004), Y. Sakamoto, K. Nagata, K. Yogo, K. Yamada, *Preparation and $CO_2$ separation properties of amine-modified mesoporous silica membranes*, Microporous and Mesoporous Materials, 101 (2007), 303-311].

Some types of ceramic and polymeric membranes are taken into account below and a computation code was used to predict the level of separation of carbon dioxide based on the important design parameters such as the stage cut, the pressure ratio and the required membrane surface.

The calculations below refer to a separation unit capable of treating a rate of 100 $Nm^3/h$.

The stage cut is defined as the ratio between the permeated capacity $N_p$ and the rate to be treated $N_0$. The pressure ratio, on the other hand, is defined as the ratio between pressure in the feed end ($p_I$) and pressure in the permeate end ($p_{II}$).

In the first place, the simplest type of flow, the complete mixing, has been considered. The main hypothesis is that the concentrations of the different chemical species remain constant in the permeated end (II) and in the feed end (I). Such hypothesis is collated when the turbulence conditions inside the system are such as to homogenise the concentration, and thereby partial pressure, gradients. Table 5 shows the permeance data relating to some of the ceramic membranes taken into account (Sakamoto et al., 2007).

TABLE 5

Data related to ceramic membranes taken from Sakamoto et al. (2007). $CO_2$ separation properties of membrane samples

| Membrane | Temperature (K) | Permeance (mol/m² s Pa) $CO_2$ | $N_2$ | $CO_2$ selectivity ($CO_2/N_2$) |
|---|---|---|---|---|
| $AL_2O_3$ Substrate[a] | 298 | $1.1 \times 10^{-6}$ | $1.1 \times 10^{-6}$ | 1.0 |
| $MS/Al_2O_3(H)$[a] | 298 | $1.0 \times 10^{-7}$ | $1.4 \times 10^{-7}$ | 0.8 |
| $MS/AL_2O_3(S)$[a] | 298 | $3.4 \times 10^{-8}$ | $4.1 \times 10^{-8}$ | 0.8 |
| APS/MS/$AL_2O_3(H)$[b] | 373 | $4.7 \times 10^{-10}$ | $8.3 \times 10^{-12}$ | 50 |
| APS/MS/$AL_2O_3(S)$[b] | 373 | $1.0 \times 10^{-9}$ | $1.2 \times 10^{-12}$ | 800 |

Test gas $CO_2/N_2$ = 20/80 Measurements were carried out after [a]1 h and [b]24 h Case I: Separation Unit with Ceramic Membranes and Flow Type "Complete Mixing".

Let's consider a separation unit consisting of a ceramic membrane APS/MS/$Al_2O_3$S shown in Table 5. Two values of pressure ratio have been considered, 20 and 30 (the gas to be treated is at atmospheric pressure).

The main results are summarised in the following Table 6:

TABLE 6

Complete mixing.

| $pI/pII$ | $S(m^2)$ | $y_P$ (%) | XL (%) | Stage cut (%) |
|---|---|---|---|---|
| 20 | 1592 | 97.2 | 8.75 | 10.39 |
| 30 | 775 | 98.0 | 8.60 | 10.40 |

It may be seen that while the degree of separation of carbon dioxide is considerable (above 97%), the required membrane surface is very high.

The rate of permeated gas rich in $CO_2$ is equal to about 10% compared to the rate to be treated. In relation to the required purity level, of course it is possible to recirculate the rate in output from the separation unit mixing it to the gas to be treated, or treat it again in a subsequent unit.

It is possible to appreciate the considerable increase of the membrane surface as the required stage cut increases.

It must be noted that to obtain a high separation degree it is necessary to limit the stage cut.

Above about 17% the decrease in the $CO_2$ concentration in the permeated is unacceptable.

The flow mode in equicurrent is analysed below, where the permeated and retentate currents flow according to the same direction.

Case II: Separation Unit with Ceramic Membranes and Flow Type "Equicurrent".

Let's consider two separation units consisting of two different membranes, APS/MS/$Al_2O_3$S and APS/MS/$Al_2O_3$H, having selectivity $CO_2/N_2$ respectively 800 and 50 (Table 7). Two pressure ratio value have been considered, 20 and 30.

Table 7 shows the main results relating to membrane APS/MS/$Al_2O_3$S having selectivity equal to 800. It is seen, for example, that quite similar performance compared to the case of complete mixing flow can be achieved with a membrane surface equal to 400 $m^2$.

TABLE 7

Flow in equicurrent and ceramic membranes.

| pI/pII | S(m²) | $y_P$ (%) | XL (%) | Stage cut (%) |
|---|---|---|---|---|
| 20 | 400 | 98.6 | 8.8 | 10.15 |
| 30 | 400 | 98.4 | 5.4 | 13.47 |

The calculations were repeated for membrane APS/MS/Al₂O₃H and the performance of the two ceramic membranes was compared, the membrane surface being equal (400 m²).

Membrane APS/MS/Al₂O₃H shows it achieves a purity degree ($y_p$) clearly higher but a similar stage cut.

Case III: Separation Unit with Polymeric Membranes and Flow Type "Equicurrent".

A separation unit was considered, consisting of polymeric membranes the data of which are shown in Table 8 (Baker, 2004).

TABLE 8

Permeability in barrer ($10^{-10}$ cm³ (STP) cm/cm²sPa) of some polymers.

| | Rubbers | | Glasses | | |
|---|---|---|---|---|---|
| Gas | Silicone rubber at 25° C. ($T_g$ - 129° C.) | Natural rubber at 30° C. ($T_g$ - 73° C.) | Cellulose acetate at 25° C. ($T_g$ 40-124° C.) | Polysulfone at 35° C. ($T_g$ 186° C.) | Polyimide (UBE Industries) at 60° C. ($T_g$ > 250° C.) |
| H₂ | 550 | 41 | 24 | 14 | 50 |
| He | 300 | 31 | 33 | 13 | 40 |
| O₂ | 500 | 23 | 1.6 | 1.4 | 3 |
| N₂ | 250 | 9.4 | 0.33 | 0.25 | 0.6 |
| CO₂ | 2700 | 153 | 10 | 5.6 | 13 |
| CH₄ | 800 | 30 | 0.36 | 0.25 | 0.4 |
| C₂H₆ | 2100 | — | 0.20 | — | 0.08 |
| C₃H₈ | 3400 | 168 | 0.13 | — | 0.015 |
| C₄H₁₀ | 7500 | — | 0.10 | — | — |

The performance of a cellulose acetate membrane was compared with a polyamide one. While the purity degree obtained is lower than that obtained with the ceramic membranes, it is possible to see that the membrane surface in both cases is greatly reduced (from 400 m² to 50 m²).

An analysis of the available membranes, especially at a commercial level, allows the man skilled in the art to optimise the separation function according to the specific requirements (CO₂ concentration) and costs (related to the membrane surface and to the pressure ratio).

It is possible to perceive that the passage from one type of flow (complete mixing) to another (equicurrent, where permeate and retentate flow in the same direction) and that changing from ceramic to polymeric membranes can affect the typical parameters of the membrane unit, such as the separation degree, the required membrane surface and the stage cut.

The resulting CO₂ is then transformed into methanol according to one of the typical transformations, known to the man skilled in the art, starting from H₂O electrolytically separated into H₂ and O₂ (in this way the problem of confining the CO₂ is solved), which is thus produced from scrap material rather than from oil origin fuels.

Production of Methanol from CO₂ and H₂ in Membrane Reactors AST-CNR/ITM

Methanol may be produced following various processes. For example by a so-called low pressure process, which works at 35-55 bars and at 200-300 ° C.

Methanol currently is mainly produced as chemical reagent or solvent. The methanol market is expected to increase in view of the research on direct methanol fuel cell (DMFC) and on the methanol reformers for producing hydrogen. The catalysts used are all based on copper and the most active and steady one is based on Cu/ZnO/Al₂O₃. Table 9 shows the typical compositions of catalysts used for producing methanol from. CO₂ and H₂.

TABLE 9

Composition of catalysts for the synthesis of methanol.

| Manufacturer | Cu [%] | Zn [%] | Al [%] |
|---|---|---|---|
| BASF | 65-75 | 20-30 | 5-10 |
| Süd Chemie | 65-75 | 18-23 | 5-10 |
| ICI | 61 | 30 | 9 |

TABLE 9-continued

Composition of catalysts for the synthesis of methanol.

| Manufacturer | Cu [%] | Zn [%] | Al [%] |
|---|---|---|---|
| Du Pont | 50 | 19 | 31 |
| Haldor Topsoe | 50-60 | 21-25 | 15-28 |

Methanol production from carbon oxides and hydrogen is a balance process, thus in conventional reactors, only a share of the supply can be converted. The reactions are the following:

$$CO + 2H_2 = CH_3OH \quad DH_{298K} = -90.70 \text{ kJ/mol} \quad (1)$$

$$CO_2 + H_2 = CO + H_2O \quad DH_{298K} = +41.19 \text{ kJ/mol} \quad (2)$$

$$CO_2 + 3H_2 = CH_3OH + H_2O \quad DH_{298K} = -49.51 \text{ kJ/mol} \quad (3)$$

The best balance conditions are obtained below 180° C. and at high pressure. In any case, at these temperatures the catalysts are not very active and thus, to reach these conversions, large reactors would be needed, with large amounts of catalysts. This is the reason why alternatives to traditional reactors are being searched for the production of methanol.

Reactor with 82 Membranes AST-CNR/ITM

The operating pressure was brought to 50 bars and thereby, a membrane reactor was designed in detail, with an inner diameter of 400 mm and with 82 membranes having the inner diameter of 20 mm with catalyst outside the membrane shown in FIG. 17, which shows the reactor with 82 membranes AST-CNR/ITM for the production of methanol from synthesis of $CO_2+H_2$.

The dimensions of the membranes are typically of 1000 mm height, with inner hole of 20 mm diameter and wall thickness of 4 mm (thickness varies as the operating pressure varies). FIG. 17 shows, besides the pack of the 82 membranes 177, also the spacing plates 175 with the indication of the holes 176 wherein the membranes are inserted.

The catalyst of the reactor is placed in plates 175 of FIGS. 17.1 and 17.2, which for this specific reactor is 107 kg; about 18 kg catalyst are therefore distributed in each plate.

In its operating position, the reactor can be seen in FIG. 17.4.

The central body of the reactor is set up with 1500 membranes and consists of 17 bundles of 82 membranes 1000 mm long, with inner diameter of 20 mm and wall thickness of 4 mm. The assembly of the membrane reactors has thus been made modular considering the one with 82 membranes as base module.

The operating pressure is 50 bar.

Methanol may be mixed with water in any proportion: mixing causes a volume shrinkage of the solution and releases heat. It is used as additive to fuels or it is used as a fuel itself, generally solid fuel (meta tablets).

In the chemical industry, it is used as solvent for dies, adhesives, polyesters, die removers, and in organic chemistry it is an important methylating agent.

Unlike ethanol, pure methanol (99%) can be obtained from an aqueous solution by a broken up distillation, whereas for absolute methanol (99.97%) the methanol must be distilled on metallic magnesium, which dissolves with the formation of magnesium alcoholate. In the presence of water, it separates to give magnesium oxide (insoluble in water) and methanol:

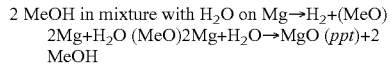

2 MeOH in mixture with $H_2O$ on Mg→$H_2$+(MeO)
2Mg+$H_2O$ (MeO)2Mg+$H_2O$→MgO (ppt)+2 MeOH Description of the AST-CNR/ITM Technology for the Industrial Preparation of Hydrogen The main technologies for hydrogen production are:
water electrolysis;
reaction of a metal with an acid
steam reforming of methane gas;
partial non catalytic oxidation of hydrocarbons;
coal gasification;
biomass gasification and pyrolysis.

Such technologies differ both in the way the bond that links hydrogen to oxygen in water is separated by electrolysis and photo-electrolysis or to carbon in hydrocarbons and biomasses, and for the raw materials used to produce hydrogen.

The removal of pollutants containing sulphur oxides in the flue gas of large plants that use fossil fuels in their processes, takes place with the formation of large amounts of sulphuric acid.

In the AST-CNR/ITM process, metal iron filling is reacted in an aqueous solution of sulphuric acid, obtaining iron sulphate and gaseous hydrogen that must then be dried, that is, freed from steam, according to the reaction

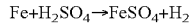

$Fe+H_2SO_4 \rightarrow FeSO_4+H_2$ 1,000 m³ gas treated with 7.40 g dipropylamine (DPA) produce 430 g $H_2SO_4$ in a solution containing 352 g $H_2$.

Examining a coal dust thermo-electrical plant 1320 MW the following amounts of materials are obtained:

4,600,000 m³/h gas treated using 34 kg/h DPA and the production of 1,981 kg/h $H_2SO_4$ in a 45% solution of $H_2O$.

A part of the hydrogen required by the "system" may be produced using $H_2SO_4$ obtained from the removal of pollutants from the flue gas.

For the production of hydrogen required for methanol synthesis, the electrolysers available on the market were used, and the same applies to the compression units, handling pumps and any other equipment required for the process.

The electrolyser HYDROPURE SESPI, selected by AST-CNR/ITM for the production of hydrogen required for methanol synthesis, is on the market.

The hydrogen and oxygen produced are stored in 2 gas meters (not shown) respectively that allow constant feeding to the purification, drying and compression systems (not shown). The purification uses the catalytic systems (in se known) that allow the production of hydrogen at 99.999% purity. Membrane or dry piston compressors (in se known) ensure a high gas purity. The gas "dew-point" is kept and controlled automatically to a dew point of about 60° C.

The production of the hydrogen required for the synthesis of methanol implies a consumption of electric energy that must be supplied to the "ZERO EMISSION AST-CNR/ITM SYSTEM".

This electric energy can be produced from renewable energy systems: wind, photovoltaic, hydroelectric or energy produced using the waste of caloric energy of the entire plant being treated.

A technology that seems to be made ad hoc for the production of hydrogen is that of photovoltaic solar panels.

All the "alternative" production systems (thermal solar, wind, geo-thermal) would in any case benefit from the production of hydrogen.

More suitable and advantageous is the production of hydrogen in thermo-electrical plants since the energy produced in excess in low requirement periods, especially in night hours, may be added to the energies listed above.

The processes described above allow operating waste free and allowing a full use of the flue gases, and thus realising a substantially zero emission plant.

The plant according to the present invention and the related reaction towers consist of modules sized so as to ensure transportability on road and railway since their dimensions are within the allowed limits without needing special authorisations for transport.

This allows simple, quick, safe and inexpensive construction of the pollutant removal plants, since these modules can be prefabricated, which also allows making custom solutions according to the plant requirements and to the type of removal to be carried out.

The removal plants according to the invention may be used in thermo-electrical plants, refineries, incinerators. Advantageously, the modular elements may be replaced in short time without expensive plant stoppage.

The reaction towers can operate with pressures up to 10 bars and allow great saving in the construction step for the reduced dimensions of the modules and in the maintenance step, made easier by the small size; moreover, they facilitate the upgrading of existing plants since the component modules are of reduced dimensions compared to those replaced and thus require less availability of space for their erection on site.

The towers of the invention allow removing the pollutants so as to permit the elimination of all the polluting matters from the flue gases and the transformation in secondary raw materials such as to be sold, or commercially pure and reusable so as not to make further waste to be removed in other forms.

The towers of the invention allow operating at "zero emissions" since it is possible to also capture the $CO_2$ and transform it into methanol, thus eliminating the problem of confining the $CO_2$ in marine or ground depths.

Combining the modular plant of the invention with thermoelectrical plants has the following further economic advantages. From recent estimates, a traditional plant sells about 62.4% of the energy it can produce, whereas the remaining 37.6% actually is a cost required to operate the plant itself. Associating the plant of the invention to the plant allows a further 7% approx. to be used for the production of secondary raw materials, first of all methanol, and the balance 30% of the energy can be used for the production of hydrogen, also sellable, besides as described above, usable for producing further methanol, with an overall efficiency that exceeds 90% and with the further advantage that such increase is not to the disadvantage but provides a large reduction of pollution.

BIBLIOGRAPHY

[1]. Struis, R. P. W. J. Stucki, S. and Wiedorn, M. (1996) A membrane reactor for methanol synthesis. J. Membrane Sci., 113: 93-100.
[2]. Rahimpour, M. R. and Ghader; S. (2004) Enhancement of CO conversion in a novel Pd—Ag membrane reactor for methanol synthesis. Chem. Eng. Proc., 43(9): 1181-1188.
[3]. Struis, R. P. W. J. and Stucki, S. (2001) Verification of the membrane reactor for methanol synthesis. Appl. Catal. A: General, 216: 117-129.
[4]. Chen, G. and Yuan, Q. (2004) Methanol synthesis from $CO_2$ using a silicone rubber/ceramic composite membrane reactor, Sep. and Pur. Techn., 34: 227-237.
[5]. Barbieri, G. Marigliano, G. Golemme, G. and Drioli, E. (2002) Simulation of $CO_2$ hydrogenation with CH3OH removal in zeolite membrane reactor. Chem. Eng. J., 85(1): 53-59
[6]. Gallucci, F. Paturzo, L. and Basile, A. (2004) An experimental study of $CO_2$ hydrogenation into methanol involving a zeolite membrane reactor. Chem. Eng. Proc., 43: 1029-1033.
[7]. S. Nair, Z. Lai, V. Nikolakis, G. Xomeritakis, G. Bonilla and M. Tsapatsis, Separation of close-boiling hydrocarbon mixtures by MFI and FAU membranes made by secondary growth, Micropouros and Mesopouros Materials 48 (2001) 219.
[8]. J. Coronas, and J. Santamaria, Separations using zeolite membranes, Sep. Purif. Meth. 28 (1999) 127.
[9]. Y. Morigami, M. Kondo, J. Abe, H. Kita, K. Okamoto, The first large-scale pervaporation plant using tubular-type module with zeolite A membrane, Sep. Purif. Technol. 25 (2001) 251.
[10]. Caro J, Noack M, Kolsch P, Schafer R. Microp & Mesop Mater 2000, 38:3-24.

The invention claimed is:
1. A plant comprising
at least one reaction tower comprising a plurality of sections arranged along a longitudinal axis for treating a gas flow,
the plurality of sections of the at least one reaction tower comprising:
a first section for treatment of fine particulates comprising dusts with diameters from 100 μm to 0.01 μm, for removal of mercury, and optionally for the further removal of one or more other heavy metals chosen from the group of: halogenides; chlorides; and fluorides;
a second section for treatment of pollutants containing sulphur oxides, and optionally aromatic hydrocarbons;
a third section for treatment of pollutants containing nitrogen oxides, and optionally aromatic hydrocarbons; and
a fourth section for capture and purification of carbon dioxide;
wherein the at least one reaction tower has a central main duct extending along the longitudinal axis, and through each section in the plurality of sections, for passage and treatment of the gas flow in each section of the plurality of sections;
wherein each of the first, second, third, and fourth sections includes: a gas flow inlet for introduction of the gas flow; a gas flow outlet for exit of the gas flow; a reagent inlet for introduction of a reagent to the gas flow; and a discharge outlet for discharge of an effluent, a reaction by-product, or both an effluent and a reaction by-product from the gas flow; and
wherein at least one of the sections in the plurality of sections is a modular section releasably mounted to the at least one reaction tower.
2. A plant according to claim 1, further comprising a section for hydrogen production and a section for methanol production.
3. A plant according to claim 1, comprising a reaction tower configured for use as a pilot plant.
4. A plant according to claim 1, comprising a plurality of reaction towers arranged in one or more groups of three reaction towers each, with the reaction towers in each group connected to each other by a smoke distribution system.
5. A plant according to claim 4, comprising 60 reaction towers arranged in groups of three reaction towers each, the groups arranged in two rows of ten stations facing each other.
6. A plant according to claim 1, comprising a prefabricated bearing structure housing the at least one reaction tower and a foundation plate, wherein
the bearing structure comprises erected frames carrying support surfaces for the various sections of the at least one reaction tower, and
the foundation plate comprises reinforced concrete.
7. A plant according to claim 1, comprising a control and acquisition system for automatically managing data gathered by the plurality of sections of the at least one reaction tower,
wherein the control and acquisition system is configured to communicate with probes arranged in the plurality of sections of the at least one reaction tower for enabling automatic performance of zero calibration measures and safety procedures.
8. A plant according to claim 1, wherein the first section of the at least one reaction tower has a cylindrical shape with diameter of 2400 mm to 2500 mm and height of about 8500 mm, operating pressure tolerance of 5 bars, and comprises an electrostatic removal device for removing fine particulates.
9. A plant according to claim 8 wherein the electrostatic removal device is positioned above a heat exchanger for incoming gas flow and comprises at least one sprinkler washing plant, a tube bundle, and an electrostatic precipitator, all enclosed in a skirt panel that is openable for inspection and maintenance.
10. A plant according to claim 8 further comprising a device for the treatment of mercury present in the gas.
11. A plant according to claim 9 wherein the tube bundle is divided into at least two modular symmetrical portions presenting a plurality of ducts or tubes with circular or prismatic sections, the modular symmetrical portions seating electrodes that are connected to support structures and current feeding systems.

12. A plant according to claim 9 wherein each sprinkler comprises a support structure whereto there is connected a feeding pipe which feeds washing liquid to the nozzles; the support structure being realized with a quadrangular element connected to a concentric cross element; the washing liquid feeding pipe being composed of main pipes wherefrom a plurality of secondary pipes branch off at 90°, parallel to each other and with different length whereon the nozzles are placed.

13. A plant according to claim 9 wherein the skirt is openable for extracting the entire tube bundle, or only a part thereof if the bundle is divided into two specularly symmetrical elements, such that once the tube bundle or a part thereof has been removed it is possible to access an inside of the section for required repairs.

14. A plant according to claim 9 wherein the tube bundle is a heat recovery tube bundle wherein the skirt is provided with a thermal recovery jacket.

15. A plant according to claim 10 wherein the mercury treatment device comprises, in a sequence from the bottom: water tanks and reaction reagents for mercury, a mercury treatment zone with one or more ceramic cylinders, and sprinkler devices.

16. A plant according to claim 1 wherein the second section of the at least one reaction tower comprises a $SO_x$ removal device comprising
a plurality of catalyst packs suitable for treating the $SO_2$ contained in the gas flow, which is absorbed on an absorbent, for regeneration to release liquid $SO_2$, sulphuric acid ($H_2SO_4$), or finally pure sulphur, and
sprinkler devices arranged at the top of the catalyst packs, wherein
the absorbent is held on solid supports positioned for drizzling by the sprinkler devices with water containing an amine, which is optionally dipropylamine.

17. A plant according to claim 1 wherein
the third section of the at least one reaction tower comprises a device for gas flow denitrifying comprising a plurality of catalyst packs and sprinkler devices arranged at the top of the catalyst packs, the catalyst packs being positioned in the flow path of the gas flow such that the gas flow will be placed in contact with the catalyst.

18. A plant according to claim 1 wherein the fourth section of the at least one reaction tower comprises a device for absorbing and capturing $CO_2$ by amine compounds kept in solution with water and sprayed by sprinkler plants on the gas flow.

19. A plant according to claim 18 wherein
the fourth section of the at least one reaction tower comprises a membrane device for absorbing and capturing $CO_2$, and separating the $CO_2$ from a gaseous inlet current composed of $N_2$ and $CO_2$,
the membrane device comprising a membrane selected from polymeric membranes, and ceramic membranes.

20. A plant according to claim 18 configured to catalytically react the captured $CO_2$ with hydrogen in membrane reactors in the presence of zeolites at a temperature within 230-:-240° C. for obtaining methanol.

21. A plant according to claim 20 configured to produce hydrogen by thermochemical separation in a device comprising an electrostatic precipitator, a furnace, a device for producing and feeding $CO_2$, an exchanger device, and a series of sulphur-iodine reactors.

22. A process for treating a gas flow produced in a plant, the plant comprising:
at least one reaction tower comprising a plurality of sections arranged along a longitudinal axis for treating a gas flow,
the plurality of sections of the at least one reaction tower comprising:
a first section for treatment of fine particulates comprising dusts with diameters from 100 μm to 0.01 μm, for removal of mercury, and optionally for the further removal of one or more other heavy metals chosen from the group of: halogenides; chlorides; and fluorides;
a second section for treatment of pollutants containing sulphur oxides, and optionally aromatic hydrocarbons;
a third section for treatment of pollutants containing nitrogen oxides, and optionally aromatic hydrocarbons; and
a fourth section for capture and purification of carbon dioxide;
wherein the at least one reaction tower has a central main duct extending along the longitudinal axis, and through each section in the plurality of sections, for passage and treatment of the gas flow in each section of the plurality of sections;
wherein each of the first, second, third, and fourth sections includes: a gas flow inlet for introduction of the gas flow; a gas flow outlet for exit of the gas flow; a reagent inlet for introduction of a reagent to the gas flow; and a discharge outlet for discharge of an effluent, a reaction by-product, or both an effluent and a reaction by-product from the gas flow; and
wherein at least one of the sections in the plurality of sections is a modular section releasably mounted to the at least one reaction tower,
the process comprising:
conducting the gas flow through the main duct of the reaction tower so as to pass the gas flow through the plurality of sections, such that the gas flow is subject to the respective treatment in each of the first, second, third, and fourth sections of the reaction tower,
producing hydrogen, and
producing methanol from the produced hydrogen and $CO_2$ captured by the fourth section of the reaction tower,
wherein mercury is removed in the first section of the reaction tower, and
wherein treatment in each of the first, second, third, and fourth sections includes: introduction of the gas flow through a gas flow inlet, introduction of a reagent through a reagent inlet, exit of the gas flow through a gas flow outlet; and discharge of an effluent, a reaction by-product, or both an effluent and a reaction by-product through a discharge outlet.

23. A process according to claim 22 wherein the gas flow is treated in the first section of the reaction tower for removal of mercury according to the Outokumpu method.

24. A process according to claim 22 wherein the gas flow is treated in the first section for removal of mercury according to the Boliden Norzink method, which includes the following stages:
circulating a mercuric chloride solution in the first section of the reaction tower, the first section comprising a plurality of concentric porous ceramic rings;
contacting the gas flow containing mercury with mercuric chloride absorbed on the ceramic rings, by passing the gas flow over the ceramic rings in the first section of the reaction tower, for forming mercurous chloride which precipitates in the mercuric chloride solution and yields a clarified mercuric chloride solution;

passing the gas flow through the ceramic rings to a further region in the plurality of sections;

flowing the clarified solution to a tank where mercurous chloride is added to the clarified solution to yield a renewed mercuric chloride solution, and pumping such renewed solution to a reagent tower to permit a continued cycle of circulating the mercuric chloride solution;

flowing solids gathered on the bottom of the tank to a decanter, where zinc powder is optionally added to favour precipitation of mercury in the mercuric chloride solution; and discharging the solids from the decanter to external stores.

25. A process according to claim 24 wherein, after treatment in the first section of the reaction tower, the gas flow is treated in the second section by adsorption on an absorbent, and regeneration of the absorbent to release liquid $SO_2$, sulphuric acid ($H_2SO_4$), or pure sulphur, and the absorbent is positioned on solid supports that are drizzled with water containing an amine, the amine optionally being dipropylamine.

26. A process according to claim 25 wherein, after treatment in the second section of the reaction tower, the gas flow is treated in the third section by a denitrifying process by contact with catalysts impregnated with ammonia, an amine, or both an ammonia and an amine to obtain a gaseous current comprising $N_2$ and $CO_2$ as an output from the third section, and the amine, if used, is optionally dipropylamine.

27. A process according to claim 26, wherein the denitrifying process comprises the steps of:

obtaining a molar ratio $NO/NO_2$ equal to about 1 in the gas flow by sending a share of the gas flow to an ancillary unit wherein ammonium nitrate is generated by contact of the share of gas flow with ammonia, amine, or both ammonia and amine, and the ammonium nitrate is reacted with $H_2SO_4$ and converted into $NO_2$; and returning about 50% of the $NO_9$ from the ancillary plant to the gas flow in the main duct of the reaction tower at a point following treatment in the second section for adjusting the ratio $NO/NO_2$ to a value of about 1; and sending the balance $NO_2$ to a complementary unit for conversion into $HNO_3$, and subsequent absorption, to produce nitric acid.

28. A process according to claim 26 wherein, in the fourth section of the reaction tower, following treatment of the gas flow in the third section, $CO_2$ is captured from the gas flow by amine compounds, the capture of $CO_2$ comprising the steps of:

spraying the gas flow with an amine solution so as to capture the $CO_2$ and modify the concentration values of the amine solution;

collecting the sprayed amine solution in a lower tank forming the bottom of the fourth section; and pumping the collected $CO_2$-enriched amine solution to a stripping unit where a heat exchanger heats the $CO_2$-enriched amine solution together with steam provided by complementary equipment to release $CO_2$; and regenerating the amine solution, and pumping the regenerated amine solution to a complementary feeding unit, the lower tank includes:

vertical walls comprising a skirt and a gas flow inlet duct;

an open top through which the sprayed amine solution falls into the lower tank for collection;

an umbrella configured for preventing the sprayed amine solution from falling into the main duct and promoting a turbulent flow of the gas flow; and floats and pressure sensors for preventing the collected amine solution from overflowing into the main duct.

29. A process according to claim 26 wherein in the fourth section of the reaction tower, following treatment of the gas flow in the third section, $CO_2$ is captured from the gas flow by a membrane device that separates the $CO_2$ from the gaseous current comprising $N_2$ and $CO_2$ output from the third section, and the membrane device comprises polymeric membranes or ceramic membranes.

30. A process according to claim 29 wherein the captured $CO_2$ is catalytically combined with hydrogen in membrane reactors in the presence of zeolites at a temperature within 230-:-240° C to obtain methanol and water that condense in the pores of the zeolites and are selectively separated from the reaction environment.

31. A process according to claim 30 wherein the hydrogen is produced by thermo-chemical separation starting from sulphuric acid and hydroiodic acid, the separation producing on one side iodine and hydrogen, and on another side sulphurous anhydride, water, and oxygen;

by-products of the hydrogen production are used in an exothermic reaction of iodine with sulphurous anhydride in the presence of water to form new sulphuric acid and hydroiodic acid, with the sulphuric acid and hydroiodic acid being put back into circulation; and the remaining reaction by-products of oxygen and heat at a temperature of about 100° C. are recycled for a further heating application.

32. A process according to claim 31 wherein at least a part of the heat required for the thermo-chemical reaction is obtained from burning unburnt coal from process waste of another unit.

33. A process according to claim 31 wherein $CO_2$ is used as a carrying fluid in heat exchangers located downstream of the combustion stage of unburnt coal.

* * * * *